US011792587B1

(12) United States Patent
Gustafsson

(10) Patent No.: US 11,792,587 B1
(45) Date of Patent: Oct. 17, 2023

(54) MAGNETIC RETENTION DEVICE

(71) Applicant: Cochlear Limited, Macquarie University (AU)

(72) Inventor: Johan Gustafsson, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 18/072,774

(22) Filed: Dec. 1, 2022

Related U.S. Application Data

(63) Continuation of application No. 17/973,930, filed on Oct. 26, 2022, which is a continuation of application No. 15/161,750, filed on May 23, 2016.

(60) Provisional application No. 62/185,288, filed on Jun. 26, 2015.

(51) Int. Cl.
   *A61N 1/36* (2006.01)
   *H04R 25/00* (2006.01)
   *A61N 1/375* (2006.01)

(52) U.S. Cl.
   CPC ........ *H04R 25/606* (2013.01); *A61N 1/37518* (2017.08); *H04R 2460/13* (2013.01)

(58) Field of Classification Search
   CPC ................... A61B 34/73; A61B 34/76; A61B 2017/000026; A61B 2017/00283; A61B 2017/00477; A61B 2034/2051; A61B 2034/2063; A61B 2034/302; A61B 2090/065; H04R 25/606; H04R 2225/67; H04R 2460/13
   See application file for complete search history.

(56) References Cited

U.S. PATENT DOCUMENTS

| | | |
|---|---|---|
| 3,043,000 A | 7/1962 | Hatfield |
| 3,487,403 A | 12/1969 | Pihl |
| 3,573,812 A | 4/1971 | Pihl |
| D227,118 S | 6/1973 | Muraoka |
| 3,771,685 A | 11/1973 | Micallef |
| 3,801,767 A | 4/1974 | Marks |
| 3,987,967 A | 10/1976 | Kuznetsov et al. |
| 4,003,521 A | 1/1977 | Hess |
| 4,038,990 A | 8/1977 | Thompson |
| 4,197,840 A | 4/1980 | Beck et al. |

(Continued)

FOREIGN PATENT DOCUMENTS

| | | |
|---|---|---|
| AU | 2009101370 A4 | 3/2013 |
| CN | 2411869 Y | 12/2000 |

(Continued)

OTHER PUBLICATIONS

Daniel Rutter, "Comparison: Lightwave 2000, 3000,4000, Illuminator and Pocket-Bright, and Petzl Tikka" pp. 1-30, Feb. 14, 2002. http://www.dansdata.com/ledlights7.htm.

(Continued)

*Primary Examiner* — Amir H Etesam
(74) *Attorney, Agent, or Firm* — Pilloff Passino & Cosenza LLP; Martin J. Cosenza

(57) ABSTRACT

An apparatus, including an external component of a medical device configured to generate a magnetic flux that removably retains, via a resulting magnetic retention force, the external component to a recipient thereof, wherein the external component is configured to enable the adjustment of a path of the generated magnetic flux so as to vary the resulting magnetic retention force.

30 Claims, 31 Drawing Sheets

(56) References Cited

U.S. PATENT DOCUMENTS

| | | | |
|---|---|---|---|
| 4,199,741 A | 4/1980 | Paulet | |
| 4,226,164 A | 10/1980 | Carter | |
| 4,240,428 A | 12/1980 | Akhavi | |
| 4,257,936 A | 3/1981 | Matsumoto et al. | |
| 4,317,969 A | 3/1982 | Riegler et al. | |
| 4,352,960 A | 10/1982 | Dormer et al. | |
| D267,541 S | 1/1983 | Kanemitsu | |
| 4,414,701 A | 11/1983 | Johnson | |
| 4,596,971 A | 6/1986 | Hirabayashi et al. | |
| 4,606,329 A | 8/1986 | Hough | |
| 4,610,621 A | 9/1986 | Taber et al. | |
| 4,628,907 A | 12/1986 | Epley | |
| 4,634,191 A | 1/1987 | Studer | |
| 4,676,772 A | 6/1987 | Hooven | |
| 4,726,378 A | 2/1988 | Kaplan | |
| 4,731,718 A | 3/1988 | Sheu | |
| 4,736,747 A | 4/1988 | Drake | |
| 4,743,264 A | 5/1988 | Sherva-Parker | |
| 4,792,368 A | 12/1988 | Sagawa et al. | |
| 4,817,607 A | 4/1989 | Tatge | |
| RE32,947 E | 6/1989 | Dormer et al. | |
| 4,868,530 A | 9/1989 | Ahs | |
| 4,917,504 A | 4/1990 | Scott et al. | |
| 4,918,745 A | 4/1990 | Hutchison | |
| 4,920,679 A | 5/1990 | Sarles et al. | |
| 5,014,592 A | 5/1991 | Zweig et al. | |
| 5,015,224 A | 5/1991 | Maniglia | |
| 5,096,763 A | 3/1992 | Ogata et al. | |
| 5,105,811 A | 4/1992 | Kuzma | |
| 5,183,056 A | 2/1993 | Dalen et al. | |
| 5,196,710 A | 3/1993 | Kalfaian | |
| 5,282,858 A | 2/1994 | Bisch et al. | |
| 5,314,453 A | 5/1994 | Jeutter | |
| D348,067 S | 6/1994 | Lucey et al. | |
| 5,338,287 A | 8/1994 | Miller et al. | |
| 5,360,388 A | 11/1994 | Spindel et al. | |
| 5,423,317 A | 6/1995 | Iijima et al. | |
| 5,456,654 A | 10/1995 | Ball | |
| 5,554,096 A | 9/1996 | Ball | |
| 5,603,726 A | 2/1997 | Schulman et al. | |
| 5,624,376 A | 4/1997 | Ball et al. | |
| 5,630,835 A | 5/1997 | Brownlee | |
| 5,716,407 A | 2/1998 | Knapp et al. | |
| 5,746,897 A | 5/1998 | Heimanson et al. | |
| 5,749,912 A | 5/1998 | Zhang et al. | |
| 5,757,183 A | 5/1998 | Smith et al. | |
| 5,775,652 A | 7/1998 | Crawshaw et al. | |
| 5,785,477 A | 7/1998 | McGuffey et al. | |
| 5,800,336 A | 9/1998 | Ball et al. | |
| 5,857,958 A | 1/1999 | Ball et al. | |
| 5,877,664 A | 3/1999 | Jackson, Jr. | |
| 5,897,486 A | 4/1999 | Ball et al. | |
| 5,913,815 A | 6/1999 | Ball et al. | |
| 5,945,762 A | 8/1999 | Chen et al. | |
| 5,965,282 A | 10/1999 | Baermann | |
| 5,971,334 A | 10/1999 | Crawshaw et al. | |
| 6,040,762 A | 3/2000 | Tompkins | |
| 6,073,973 A | 6/2000 | Boscaljon et al. | |
| 6,101,417 A | 8/2000 | Vogel et al. | |
| 6,138,681 A | 10/2000 | Chen et al. | |
| 6,157,278 A | 12/2000 | Katznelson et al. | |
| 6,157,281 A | 12/2000 | Katznelson et al. | |
| 6,175,767 B1 | 1/2001 | Doyle, Sr. | |
| 6,178,079 B1 | 1/2001 | Renger | |
| 6,178,353 B1 | 1/2001 | Griffith et al. | |
| 6,190,305 B1 | 2/2001 | Ball et al. | |
| 6,208,235 B1 | 3/2001 | Frontelj | |
| 6,208,882 B1 | 3/2001 | Lenarz et al. | |
| 6,217,508 B1 | 4/2001 | Ball et al. | |
| 6,219,580 B1 | 4/2001 | Faltys et al. | |
| 6,244,142 B1 | 6/2001 | Swanson | |
| 6,259,951 B1 | 7/2001 | Kuzma et al. | |
| 6,263,230 B1 | 7/2001 | Haynor et al. | |
| 6,272,382 B1 | 8/2001 | Faltys et al. | |
| 6,292,678 B1 | 9/2001 | Hall et al. | |
| 6,295,472 B1 | 9/2001 | Rubinstein et al. | |
| 6,295,473 B1 | 9/2001 | Rosar | |
| 6,308,101 B1 | 10/2001 | Faltys et al. | |
| 6,313,551 B1 | 11/2001 | Hazelton | |
| 6,348,070 B1 | 2/2002 | Teissl et al. | |
| 6,355,998 B1 | 3/2002 | Schöb et al. | |
| 6,358,281 B1 | 3/2002 | Berrang et al. | |
| 6,401,723 B1 | 6/2002 | Garibaldi et al. | |
| 6,475,134 B1 | 11/2002 | Ball et al. | |
| 6,505,062 B1 | 1/2003 | Ritter et al. | |
| 6,506,987 B1 | 1/2003 | Woods | |
| 6,522,909 B1 | 2/2003 | Garibaldi et al. | |
| 6,542,777 B1 | 4/2003 | Griffith et al. | |
| 6,571,676 B1 | 6/2003 | Folsom et al. | |
| 6,643,378 B2 | 11/2003 | Schumaier | |
| 6,668,065 B2 | 12/2003 | Lee et al. | |
| 6,838,963 B2 | 1/2005 | Zimmerling et al. | |
| 6,857,612 B2 | 2/2005 | Goodbred | |
| D512,416 S | 12/2005 | Malaver | |
| 6,991,594 B2 | 1/2006 | Holcomb | |
| 7,038,565 B1 | 5/2006 | Chell | |
| 7,091,806 B2 | 8/2006 | Zimmerling et al. | |
| 7,190,247 B2 | 3/2007 | Zimmerling | |
| 7,191,007 B2 | 3/2007 | Desai et al. | |
| 7,200,504 B1 | 4/2007 | Fister | |
| 7,225,028 B2 | 5/2007 | Della Santina et al. | |
| 7,231,252 B2 | 6/2007 | Duncan et al. | |
| 7,266,208 B2 | 9/2007 | Charvin et al. | |
| 7,338,028 B2 | 3/2008 | Zimmerling et al. | |
| 7,386,143 B2 | 6/2008 | Easter et al. | |
| 7,532,937 B2 | 5/2009 | Horio et al. | |
| 7,566,296 B2 | 7/2009 | Zimmerling et al. | |
| 7,610,096 B2 | 10/2009 | McDonald, III | |
| 7,642,887 B2 | 1/2010 | Zimmerling | |
| 7,647,120 B2 | 1/2010 | Della Santina et al. | |
| 7,695,427 B2 | 4/2010 | Kugler et al. | |
| 7,762,998 B2 | 7/2010 | Birk et al. | |
| 7,808,348 B2 | 10/2010 | Fullerton et al. | |
| 7,856,986 B2 | 12/2010 | Darley | |
| 7,976,453 B2 | 7/2011 | Zimmerling et al. | |
| 7,991,477 B2 | 8/2011 | McDonald, III | |
| 8,013,699 B2 | 9/2011 | Zimmerling | |
| 8,118,725 B2 | 2/2012 | Zimmerling et al. | |
| 8,211,174 B2 | 7/2012 | Park et al. | |
| 8,246,533 B2 | 8/2012 | Chang et al. | |
| 8,255,058 B2 | 8/2012 | Gibson et al. | |
| 8,260,435 B2 | 9/2012 | Johnson et al. | |
| 8,270,647 B2 | 9/2012 | Crawford et al. | |
| 8,340,774 B2 | 12/2012 | Hochmair et al. | |
| 8,400,038 B2 | 3/2013 | Smith et al. | |
| 8,406,443 B2 | 3/2013 | Westerkull et al. | |
| 8,515,112 B2 | 8/2013 | Crawford et al. | |
| 8,515,544 B2 | 8/2013 | Daly et al. | |
| 8,532,783 B2 | 9/2013 | Zimmerling et al. | |
| 8,634,909 B2 | 1/2014 | Zimmerling et al. | |
| 8,734,475 B2 | 5/2014 | Ekvall et al. | |
| 8,744,106 B2 | 6/2014 | Ball | |
| 8,758,394 B2 | 6/2014 | Zimmerling et al. | |
| 8,768,480 B2 | 7/2014 | Charvin | |
| 8,811,643 B2 | 8/2014 | Crawford et al. | |
| 8,829,462 B2 | 9/2014 | Clarke et al. | |
| 8,829,752 B2 | 9/2014 | Chen et al. | |
| 8,897,475 B2 | 11/2014 | Ball et al. | |
| 8,983,102 B2 | 3/2015 | Crawford et al. | |
| 8,987,951 B2 | 3/2015 | Park | |
| 9,002,469 B2 | 4/2015 | D'Ambrosio | |
| 9,014,782 B2 | 4/2015 | Miyoshi | |
| 9,022,917 B2 | 5/2015 | Kasic et al. | |
| 9,042,995 B2 | 5/2015 | Dinsmoor et al. | |
| 9,058,962 B2 | 6/2015 | Endo et al. | |
| 9,113,268 B2 | 8/2015 | Ball et al. | |
| RE45,701 E | 9/2015 | Zimmerling et al. | |
| 9,136,728 B2 | 9/2015 | Dinsmoor et al. | |
| 9,144,676 B2 | 9/2015 | Gibson et al. | |
| 9,179,228 B2 | 11/2015 | Ruppersberg et al. | |
| 9,210,521 B2 | 12/2015 | Kasic et al. | |
| 9,258,656 B2 | 2/2016 | Ruppersberg et al. | |
| 9,392,384 B2 | 7/2016 | Crawford et al. | |
| 9,420,388 B2 | 8/2016 | Ball | |

(56) References Cited

U.S. PATENT DOCUMENTS

| | | |
|---|---|---|
| 9,526,810 B2 | 12/2016 | Ruppersberg |
| 9,627,120 B2 | 4/2017 | Scott et al. |
| 9,736,601 B2 | 8/2017 | Kasic et al. |
| 9,739,842 B2 | 8/2017 | Holm et al. |
| 9,788,125 B2 | 10/2017 | Ruppersberg et al. |
| RE46,624 E | 12/2017 | Zimmerling et al. |
| 9,872,115 B2 | 1/2018 | Kennes |
| 9,872,993 B2 | 1/2018 | Zimmerling |
| 10,130,807 B2 | 11/2018 | Leigh et al. |
| 10,186,360 B2 | 1/2019 | Shimbo et al. |
| 10,405,891 B2 | 9/2019 | Pool et al. |
| 10,646,712 B2 | 5/2020 | Smith et al. |
| 10,917,730 B2 | 2/2021 | Kennes et al. |
| 10,942,042 B2 | 3/2021 | Bidaux et al. |
| 11,012,796 B2 | 5/2021 | Andersson et al. |
| 11,097,095 B2 | 8/2021 | Smith et al. |
| 2001/0021805 A1 | 9/2001 | Blume et al. |
| 2002/0076071 A1 | 6/2002 | Single |
| 2002/0103430 A1 | 8/2002 | Hastings |
| 2002/0116033 A1 | 8/2002 | Greatbatch et al. |
| 2002/0116034 A1 | 8/2002 | Miller et al. |
| 2002/0120332 A1 | 8/2002 | Law et al. |
| 2003/0034039 A1 | 2/2003 | Schmid et al. |
| 2003/0034705 A1 | 2/2003 | Hakansson |
| 2003/0089933 A1 | 5/2003 | Janesky et al. |
| 2003/0120202 A1 | 6/2003 | Gordon |
| 2003/0139782 A1 | 7/2003 | Duncan |
| 2003/0161481 A1 | 8/2003 | Miller et al. |
| 2003/0161482 A1 | 8/2003 | Miller et al. |
| 2003/0163021 A1 | 8/2003 | Miller et al. |
| 2003/0163022 A1 | 8/2003 | Miller et al. |
| 2003/0171787 A1 | 9/2003 | Money et al. |
| 2003/0171792 A1 | 9/2003 | Zarinetchi et al. |
| 2003/0181956 A1 | 9/2003 | Duncan et al. |
| 2004/0012470 A1 | 1/2004 | Zimmerling et al. |
| 2004/0032962 A1 | 2/2004 | Westerkull |
| 2004/0059423 A1 | 3/2004 | Barnes et al. |
| 2004/0136558 A1 | 7/2004 | Usuki et al. |
| 2004/0147804 A1 | 7/2004 | Schneider et al. |
| 2004/0148025 A1 | 7/2004 | Schneider et al. |
| 2004/0260361 A1 | 12/2004 | Gibson |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2005/0070346 A1 | 3/2005 | Pan |
| 2005/0101830 A1 | 5/2005 | Easter et al. |
| 2005/0159791 A1 | 7/2005 | Daly et al. |
| 2005/0165471 A1 | 7/2005 | Wang et al. |
| 2005/0171579 A1 | 8/2005 | Tasche et al. |
| 2005/0197715 A1 | 9/2005 | Kugler et al. |
| 2005/0216075 A1 | 9/2005 | Wang et al. |
| 2005/0228214 A1 | 10/2005 | Schneider et al. |
| 2005/0228215 A1 | 10/2005 | Schneider et al. |
| 2005/0240098 A1 | 10/2005 | Zhong et al. |
| 2006/0030905 A1 | 2/2006 | Malaver |
| 2006/0045298 A1 | 3/2006 | Westerkull |
| 2006/0056649 A1 | 3/2006 | Schumaier |
| 2006/0084857 A1 | 4/2006 | Massengill et al. |
| 2006/0119356 A1 | 6/2006 | Rabe et al. |
| 2006/0184212 A1 | 8/2006 | Faltys et al. |
| 2006/0217792 A1 | 9/2006 | Hussein et al. |
| 2006/0241746 A1 | 10/2006 | Shaoulian et al. |
| 2006/0244560 A1 | 11/2006 | Zimmerling et al. |
| 2006/0247488 A1 | 11/2006 | Waldmann |
| 2007/0053536 A1 | 3/2007 | Westerkull |
| 2007/0083078 A1 | 4/2007 | Easter et al. |
| 2007/0100197 A1 | 5/2007 | Perkins et al. |
| 2007/0126540 A1 | 6/2007 | Zimmerling |
| 2007/0170533 A1 | 7/2007 | Doogue et al. |
| 2007/0179333 A1 | 8/2007 | Bove |
| 2007/0208403 A1 | 9/2007 | Della Santina et al. |
| 2008/0009920 A1 | 1/2008 | Gibson et al. |
| 2008/0044049 A1 | 2/2008 | Ho et al. |
| 2008/0071353 A1 | 3/2008 | Weber et al. |
| 2008/0221641 A1 | 9/2008 | Hochmair |
| 2008/0293998 A1 | 11/2008 | Andrews |
| 2008/0304686 A1 | 12/2008 | Meskens et al. |
| 2009/0030529 A1 | 1/2009 | Berrang et al. |
| 2009/0043149 A1 | 2/2009 | Abel |
| 2009/0069869 A1 | 3/2009 | Stouffer et al. |
| 2009/0138062 A1 | 5/2009 | Balslev |
| 2009/0237080 A1 | 9/2009 | Kato et al. |
| 2009/0248155 A1 | 10/2009 | Parker |
| 2009/0251264 A1 | 10/2009 | Fullerton et al. |
| 2009/0281367 A1 | 11/2009 | Cho et al. |
| 2009/0287036 A1 | 11/2009 | Shapiro et al. |
| 2009/0287278 A1 | 11/2009 | Charvin |
| 2009/0295521 A1 | 12/2009 | Fullerton et al. |
| 2010/0145135 A1 | 6/2010 | Ball et al. |
| 2010/0219712 A1 | 9/2010 | Kogure et al. |
| 2010/0237969 A1 | 9/2010 | Crawshaw |
| 2010/0272299 A1 | 10/2010 | Van Schuylenbergh et al. |
| 2010/0292759 A1 | 11/2010 | Hahn et al. |
| 2011/0004278 A1 | 1/2011 | Aghassian |
| 2011/0022120 A1 | 1/2011 | Ball et al. |
| 2011/0031839 A1 | 2/2011 | Fullerton et al. |
| 2011/0054237 A1 | 3/2011 | Shapiro et al. |
| 2011/0077502 A1 | 3/2011 | Rofougaran |
| 2011/0106210 A1 | 5/2011 | Meskens |
| 2011/0112607 A1 | 5/2011 | Zierhofer |
| 2011/0130622 A1 | 6/2011 | Ilberg |
| 2011/0152603 A1 | 6/2011 | Perkins et al. |
| 2011/0224789 A1 | 9/2011 | Griffith |
| 2011/0264172 A1* | 10/2011 | Zimmerling ....... A61N 1/36036 607/60 |
| 2011/0268303 A1 | 11/2011 | Ahsani |
| 2011/0285488 A1 | 11/2011 | Scott et al. |
| 2011/0291507 A1 | 12/2011 | Post |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0062992 A1 | 3/2012 | Kimoto |
| 2012/0078035 A1 | 3/2012 | Andersson et al. |
| 2012/0080039 A1 | 4/2012 | Siegert |
| 2012/0088956 A1 | 4/2012 | Asnes et al. |
| 2012/0095283 A1 | 4/2012 | Andersson et al. |
| 2012/0104875 A1 | 5/2012 | Park |
| 2012/0108887 A1 | 5/2012 | Vermeiren |
| 2012/0172659 A1 | 7/2012 | Ball et al. |
| 2012/0237067 A1 | 9/2012 | Asnes |
| 2012/0238799 A1 | 9/2012 | Ball et al. |
| 2012/0256715 A1 | 10/2012 | Fullerton et al. |
| 2012/0262019 A1 | 10/2012 | Smith et al. |
| 2012/0262020 A1 | 10/2012 | Smith et al. |
| 2012/0284969 A1 | 11/2012 | Fullerton et al. |
| 2012/0296155 A1 | 11/2012 | Ball |
| 2012/0313473 A1 | 12/2012 | Chen et al. |
| 2012/0319809 A1 | 12/2012 | Fullerton |
| 2012/0323066 A1 | 12/2012 | Cho et al. |
| 2012/0330378 A1 | 12/2012 | Crawford et al. |
| 2013/0004003 A1 | 1/2013 | Tada |
| 2013/0006044 A1 | 1/2013 | Menzl |
| 2013/0018218 A1 | 1/2013 | Haller et al. |
| 2013/0023954 A1 | 1/2013 | Meskens |
| 2013/0046131 A1 | 2/2013 | Ball et al. |
| 2013/0046360 A1 | 2/2013 | Gibson et al. |
| 2013/0053874 A1 | 2/2013 | Ekvall et al. |
| 2013/0096366 A1 | 4/2013 | Bervoets et al. |
| 2013/0099703 A1 | 4/2013 | Epstein et al. |
| 2013/0110198 A1 | 5/2013 | Stoffaneller |
| 2013/0114834 A1 | 5/2013 | Bern |
| 2013/0165738 A1 | 6/2013 | Ball et al. |
| 2013/0190552 A1 | 7/2013 | Leblans |
| 2013/0195304 A1 | 8/2013 | Andersson |
| 2013/0199031 A1 | 8/2013 | Fullerton et al. |
| 2013/0202140 A1 | 8/2013 | Asnes |
| 2013/0207760 A1 | 8/2013 | Clarke et al. |
| 2013/0214631 A1 | 8/2013 | Smith et al. |
| 2013/0261701 A1 | 10/2013 | Kuratle et al. |
| 2013/0268012 A1 | 10/2013 | Sison |
| 2013/0278254 A1 | 10/2013 | Reeder et al. |
| 2013/0281764 A1 | 10/2013 | Björn et al. |

(56) References Cited

U.S. PATENT DOCUMENTS

| | | |
|---|---|---|
| 2013/0289384 A1 | 10/2013 | Jenison et al. |
| 2013/0305522 A1 | 11/2013 | Fullerton et al. |
| 2014/0005522 A1 | 1/2014 | Zurovcik |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0064531 A1 | 3/2014 | Andersson et al. |
| 2014/0094876 A1 | 4/2014 | Wingeier et al. |
| 2014/0121447 A1 | 5/2014 | Kasic et al. |
| 2014/0121450 A1 | 5/2014 | Kasic et al. |
| 2014/0121451 A1 | 5/2014 | Kasic et al. |
| 2014/0163308 A1 | 6/2014 | Miller et al. |
| 2014/0163309 A1 | 6/2014 | Bernhard et al. |
| 2014/0213139 A1 | 7/2014 | Ferguson |
| 2014/0242140 A1 | 8/2014 | Neu et al. |
| 2014/0257081 A1 | 9/2014 | Rapoport |
| 2014/0270297 A1 | 9/2014 | Gustafsson et al. |
| 2014/0275731 A1 | 9/2014 | Andersson et al. |
| 2014/0275736 A1 | 9/2014 | Ruppersberg et al. |
| 2014/0292321 A1 | 10/2014 | Yamazaki et al. |
| 2014/0293073 A1 | 10/2014 | Okamura et al. |
| 2014/0300437 A1 | 10/2014 | Fullerton et al. |
| 2014/0302741 A1 | 10/2014 | Whittaker |
| 2014/0321681 A1 | 10/2014 | Ball et al. |
| 2014/0336447 A1* | 11/2014 | Bjorn .................. H04R 25/606 600/25 |
| 2014/0343626 A1 | 11/2014 | Thenuwara et al. |
| 2014/0364681 A1 | 12/2014 | Hillbratt et al. |
| 2014/0364682 A1 | 12/2014 | Hillbratt et al. |
| 2014/0364922 A1 | 12/2014 | Garnham et al. |
| 2014/0375829 A1 | 12/2014 | Nishihara et al. |
| 2014/0379103 A1 | 12/2014 | Ishikawa et al. |
| 2015/0022298 A1 | 1/2015 | Fullerton |
| 2015/0032186 A1 | 1/2015 | Cushing et al. |
| 2015/0045607 A1 | 2/2015 | Håkansson |
| 2015/0045855 A1 | 2/2015 | Griffith |
| 2015/0087892 A1 | 3/2015 | Tourrel et al. |
| 2015/0092969 A1 | 4/2015 | Meskens et al. |
| 2015/0104052 A1 | 4/2015 | Gustafsson et al. |
| 2015/0117689 A1 | 4/2015 | Bergs et al. |
| 2015/0156595 A1 | 6/2015 | Zhong et al. |
| 2015/0157778 A1 | 6/2015 | Ishiyama et al. |
| 2015/0160426 A1 | 6/2015 | Chao et al. |
| 2015/0160470 A1 | 6/2015 | Terajima |
| 2015/0173468 A1 | 6/2015 | Stevenson |
| 2015/0192432 A1 | 7/2015 | Noguchi et al. |
| 2015/0201290 A1 | 7/2015 | Nikles et al. |
| 2015/0215708 A1 | 7/2015 | Meskens et al. |
| 2015/0265842 A1 | 9/2015 | Ridler et al. |
| 2015/0281860 A1 | 10/2015 | Johansson et al. |
| 2015/0312686 A1 | 10/2015 | Gustafsson et al. |
| 2015/0382114 A1 | 12/2015 | Andersson et al. |
| 2016/0021470 A1 | 1/2016 | Gustafsson |
| 2016/0037273 A1 | 2/2016 | Gustafsson |
| 2016/0058555 A1 | 3/2016 | Andersson et al. |
| 2016/0084920 A1 | 3/2016 | Liu et al. |
| 2016/0100260 A1 | 4/2016 | Ruppersberg et al. |
| 2016/0112813 A1 | 4/2016 | Hillbratt et al. |
| 2016/0161288 A1 | 6/2016 | Lu |
| 2016/0198270 A9 | 7/2016 | Nagl et al. |
| 2016/0205484 A1 | 7/2016 | Nagl et al. |
| 2016/0234613 A1 | 8/2016 | Westerkull |
| 2016/0247616 A1 | 8/2016 | Smith et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0078808 A1 | 3/2017 | Kennes |
| 2017/0111728 A1 | 4/2017 | Kim et al. |
| 2017/0162311 A1 | 6/2017 | Shmbo et al. |
| 2017/0162367 A1 | 6/2017 | Yokota et al. |
| 2017/0216523 A1 | 8/2017 | Neftel et al. |
| 2017/0251313 A1 | 8/2017 | Gustafsson |
| 2018/0160241 A1 | 6/2018 | Gustafsson et al. |
| 2018/0252228 A1 | 9/2018 | Henseler et al. |
| 2018/0270591 A1 | 9/2018 | Kennes |
| 2018/0288538 A1 | 10/2018 | Andersson et al. |
| 2018/0352349 A1 | 12/2018 | Fung et al. |
| 2018/0369586 A1 | 12/2018 | Lee et al. |
| 2019/0046797 A1 | 2/2019 | Calixto et al. |
| 2019/0076649 A1 | 3/2019 | Lee et al. |
| 2019/0151653 A1 | 5/2019 | Leigh et al. |
| 2019/0215623 A1 | 7/2019 | Bodvarsson |
| 2019/0239007 A1 | 8/2019 | Kennes et al. |
| 2019/0293454 A1 | 9/2019 | Bidaux et al. |
| 2020/0114151 A1 | 4/2020 | Smith et al. |
| 2020/0197702 A1 | 6/2020 | Eigentler |
| 2021/0046318 A1 | 2/2021 | Gibson et al. |
| 2021/0106815 A1 | 4/2021 | Smith et al. |
| 2021/0235209 A1 | 7/2021 | Kennes et al. |
| 2021/0257139 A1 | 8/2021 | Nellessen |
| 2021/0316136 A1 | 10/2021 | Smith et al. |
| 2022/0072302 A1 | 3/2022 | Zimmerling |

FOREIGN PATENT DOCUMENTS

| | | |
|---|---|---|
| EP | 2720480 A2 | 4/2014 |
| EP | 3307383 B1 | 3/2020 |
| GB | 414579 A | 8/1934 |
| GB | 2196855 A | 5/1988 |
| GB | 2205999 A | 12/1988 |
| GB | 2266045 A | 10/1993 |
| JP | 2010075394 A | 4/2010 |
| JP | 2012191448 A | 10/2012 |
| JP | 2013232860 A | 11/2013 |
| KR | 101743793 A | 5/2013 |
| KR | 101297828 B1 | 8/2013 |
| KR | 101537380 B1 | 7/2015 |
| WO | 9716835 A1 | 5/1997 |
| WO | 9939769 A1 | 8/1999 |
| WO | 2007024657 A1 | 3/2007 |
| WO | 2014008169 A1 | 1/2014 |
| WO | 2014011582 A2 | 1/2014 |
| WO | 2015065442 A2 | 5/2015 |
| WO | 2016207856 A1 | 12/2016 |
| WO | 2016207860 A1 | 12/2016 |
| WO | 2017046650 A1 | 3/2017 |
| WO | 2017105510 A1 | 6/2017 |
| WO | 2017105511 A1 | 6/2017 |
| WO | 2018200347 A1 | 11/2018 |
| WO | 2021059163 A1 | 4/2021 |

OTHER PUBLICATIONS

MED-EL, "FDA Hands MED-EL Approval for MRI Compatible Cochlear Implant (Video)," believed to be available in Jan. 2015.

* cited by examiner

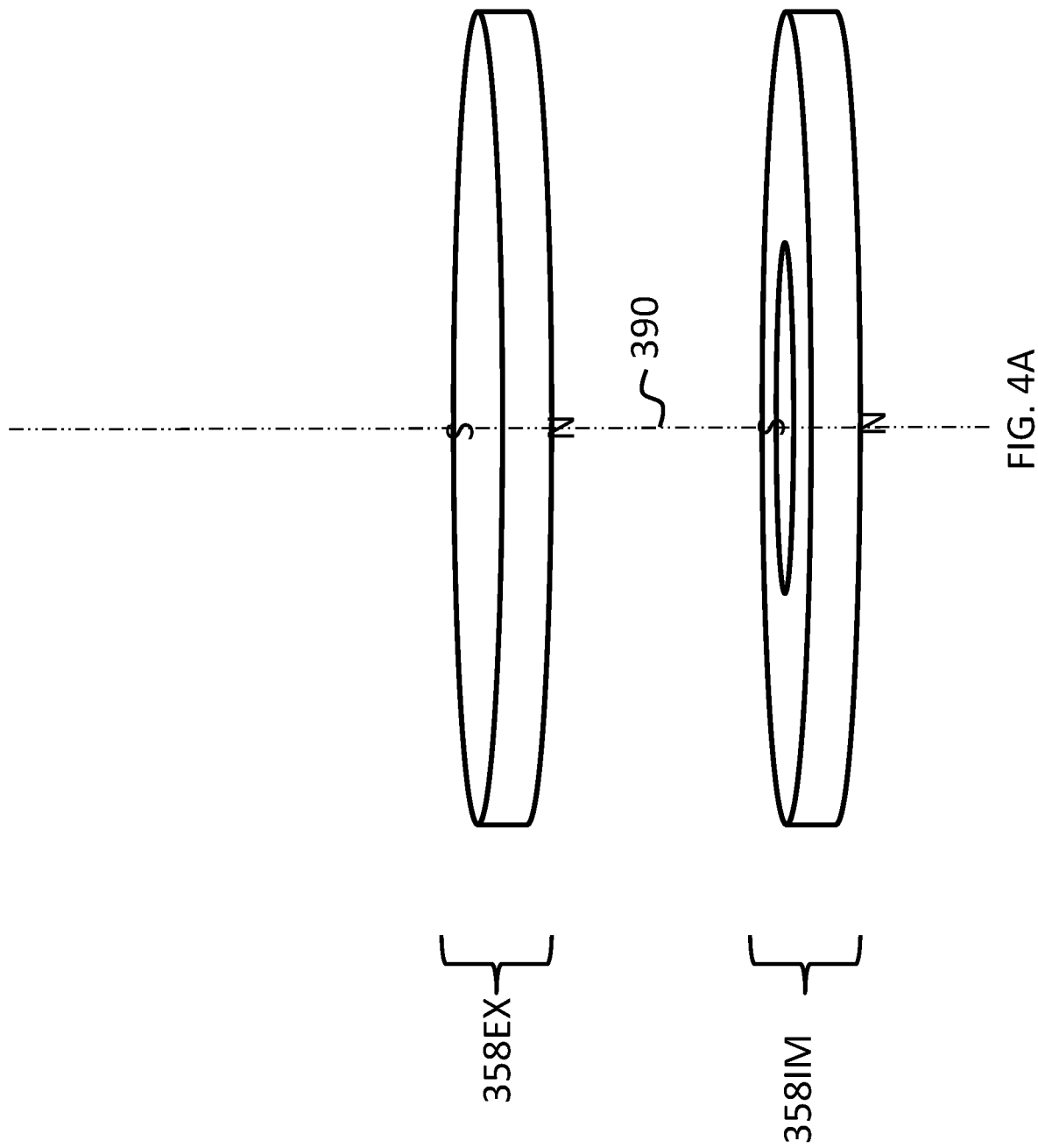

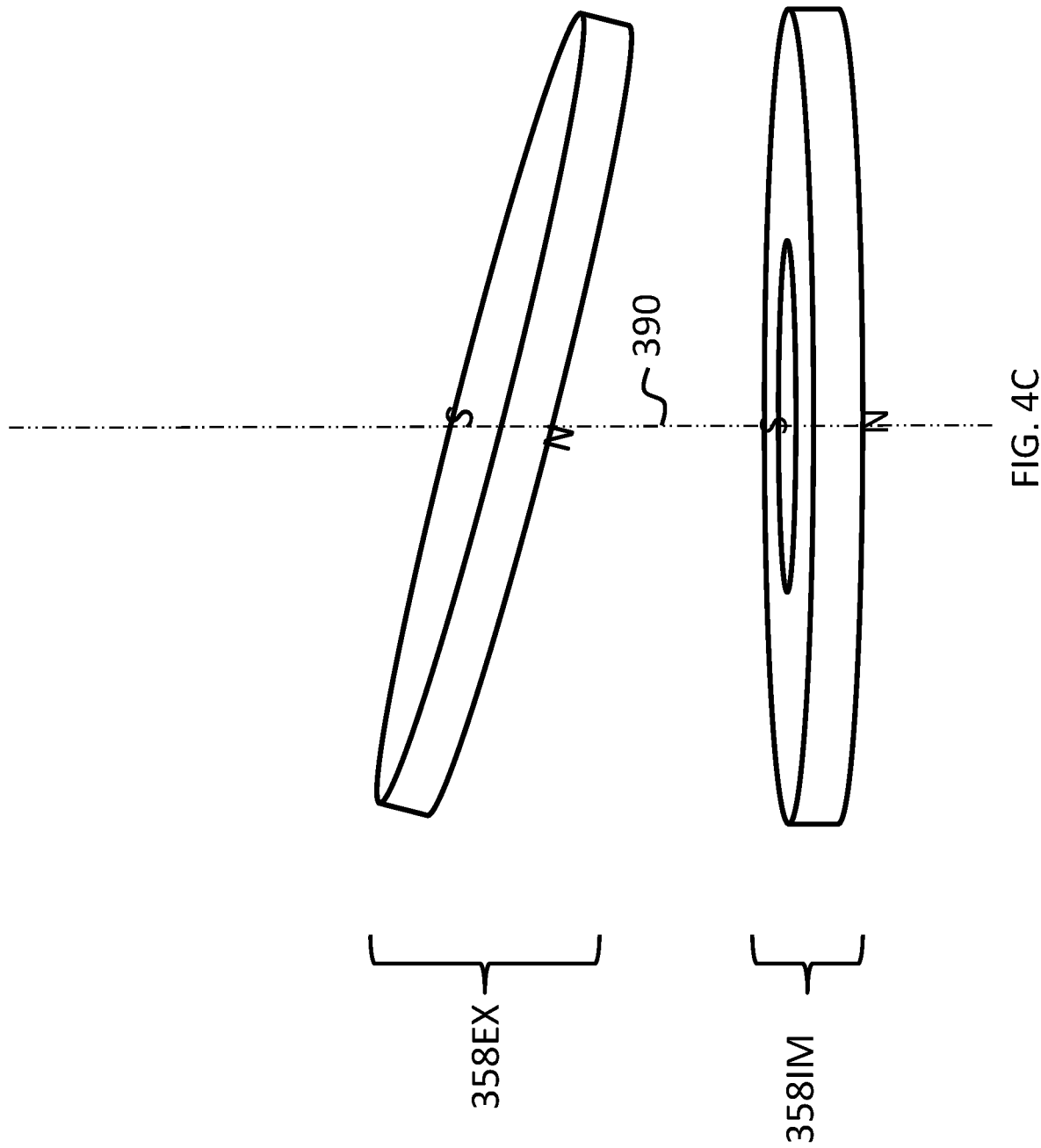

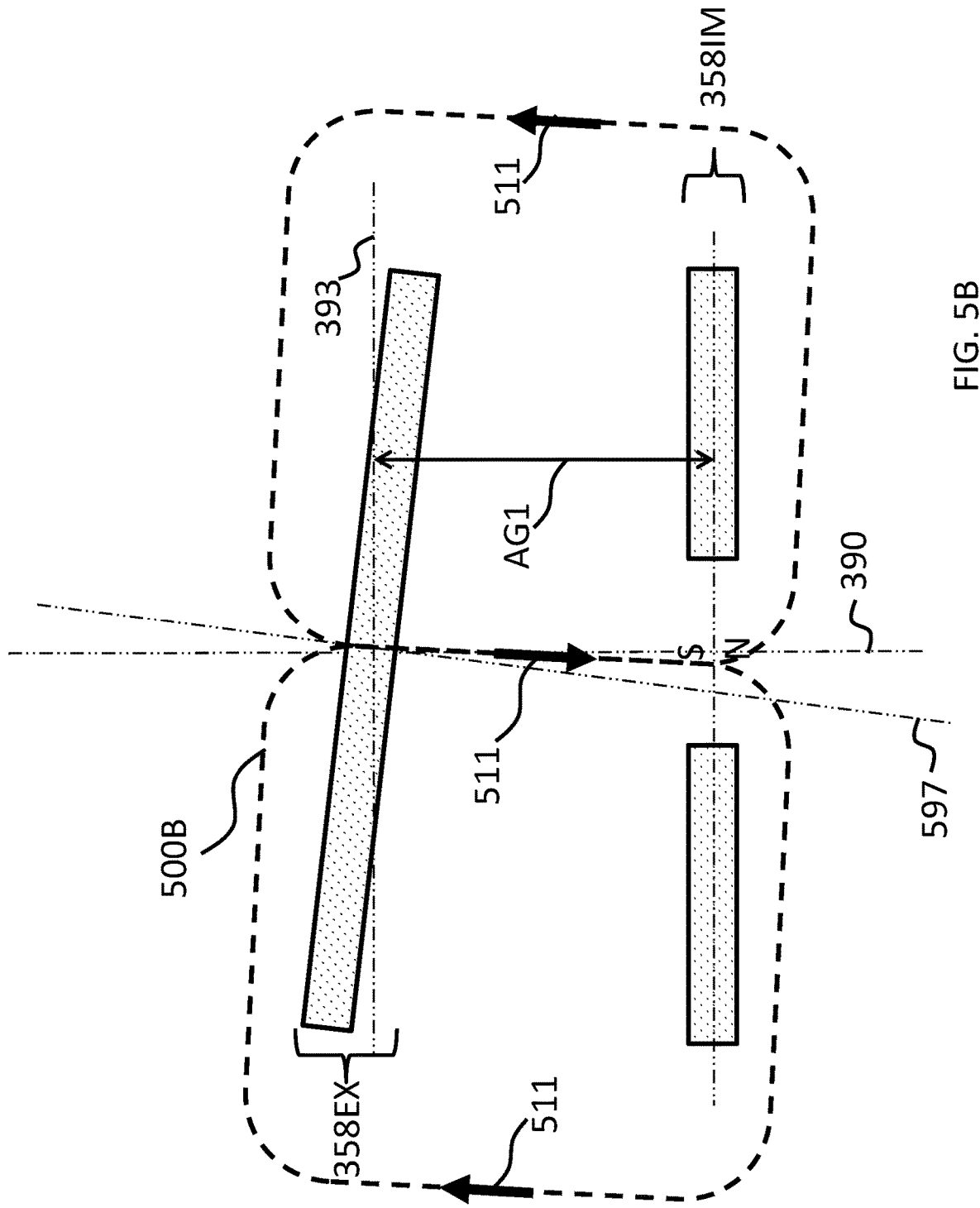

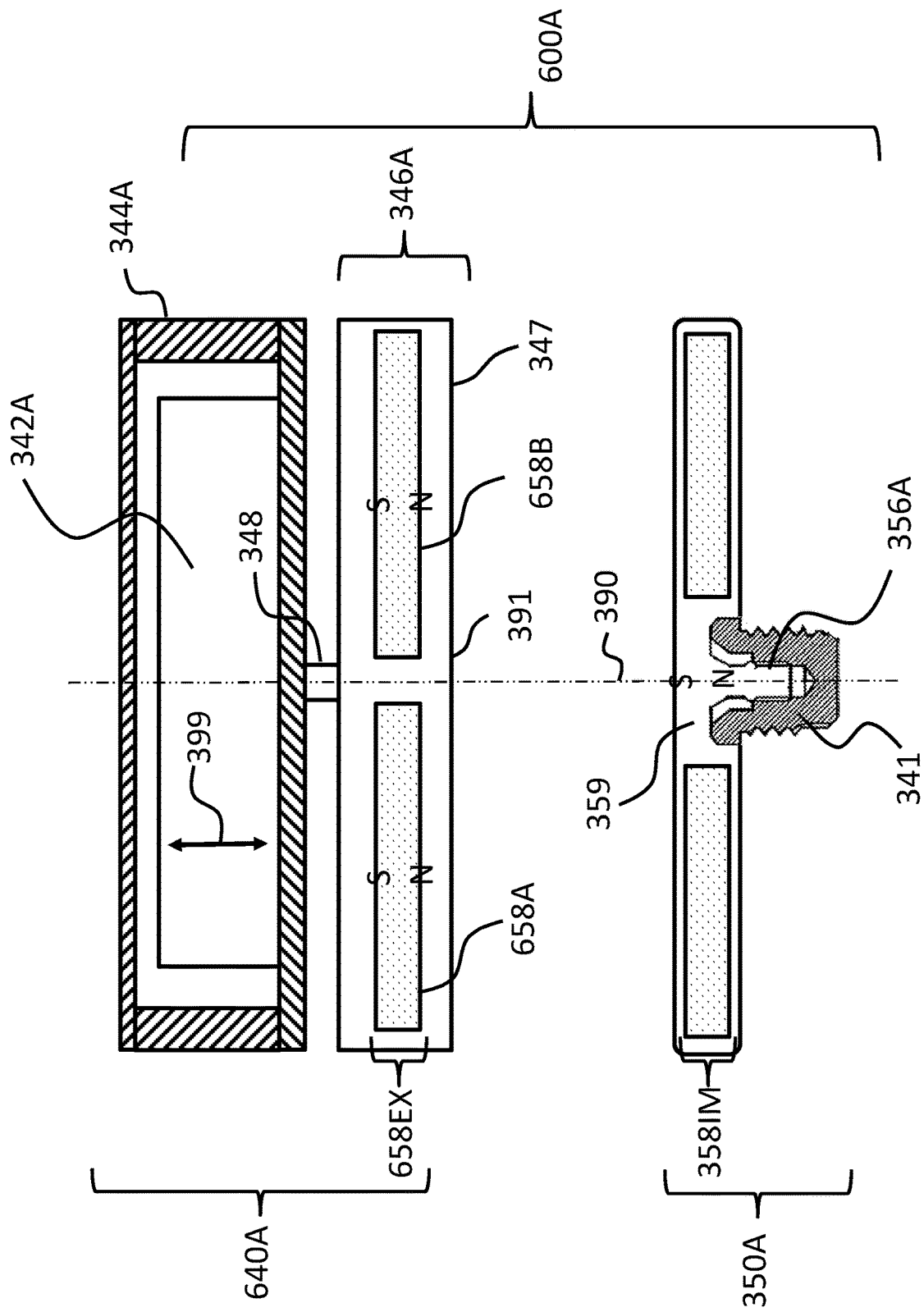

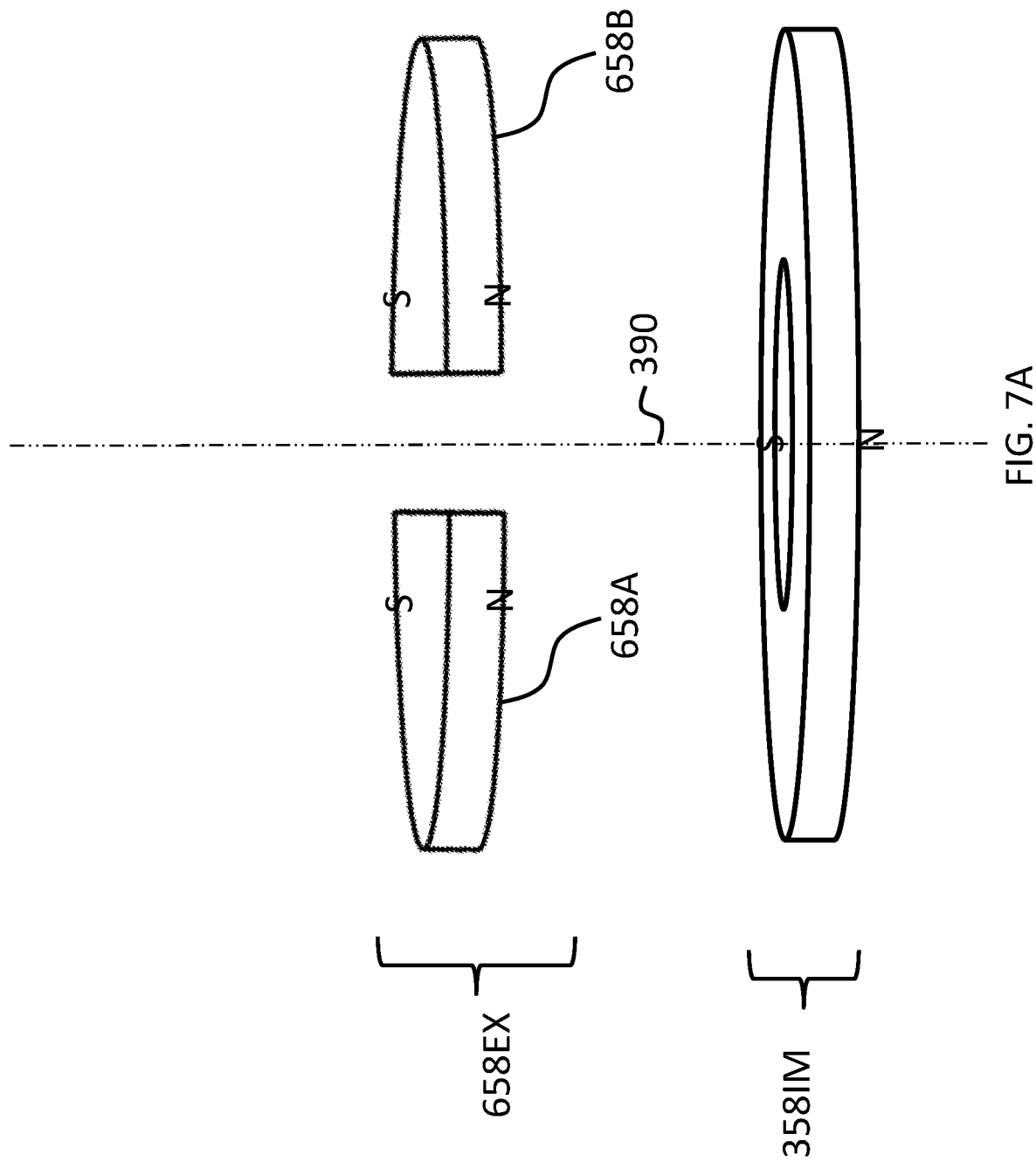

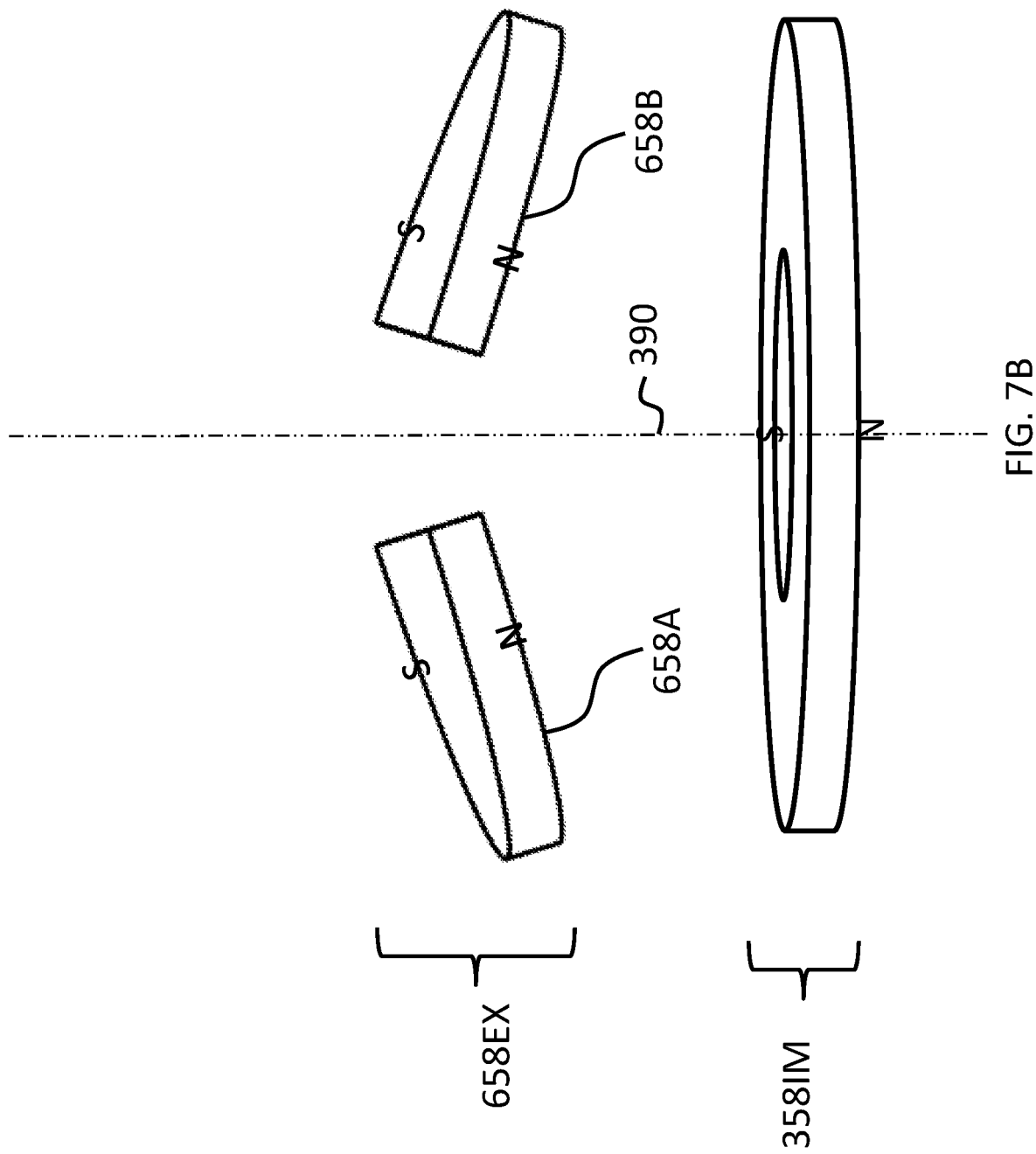

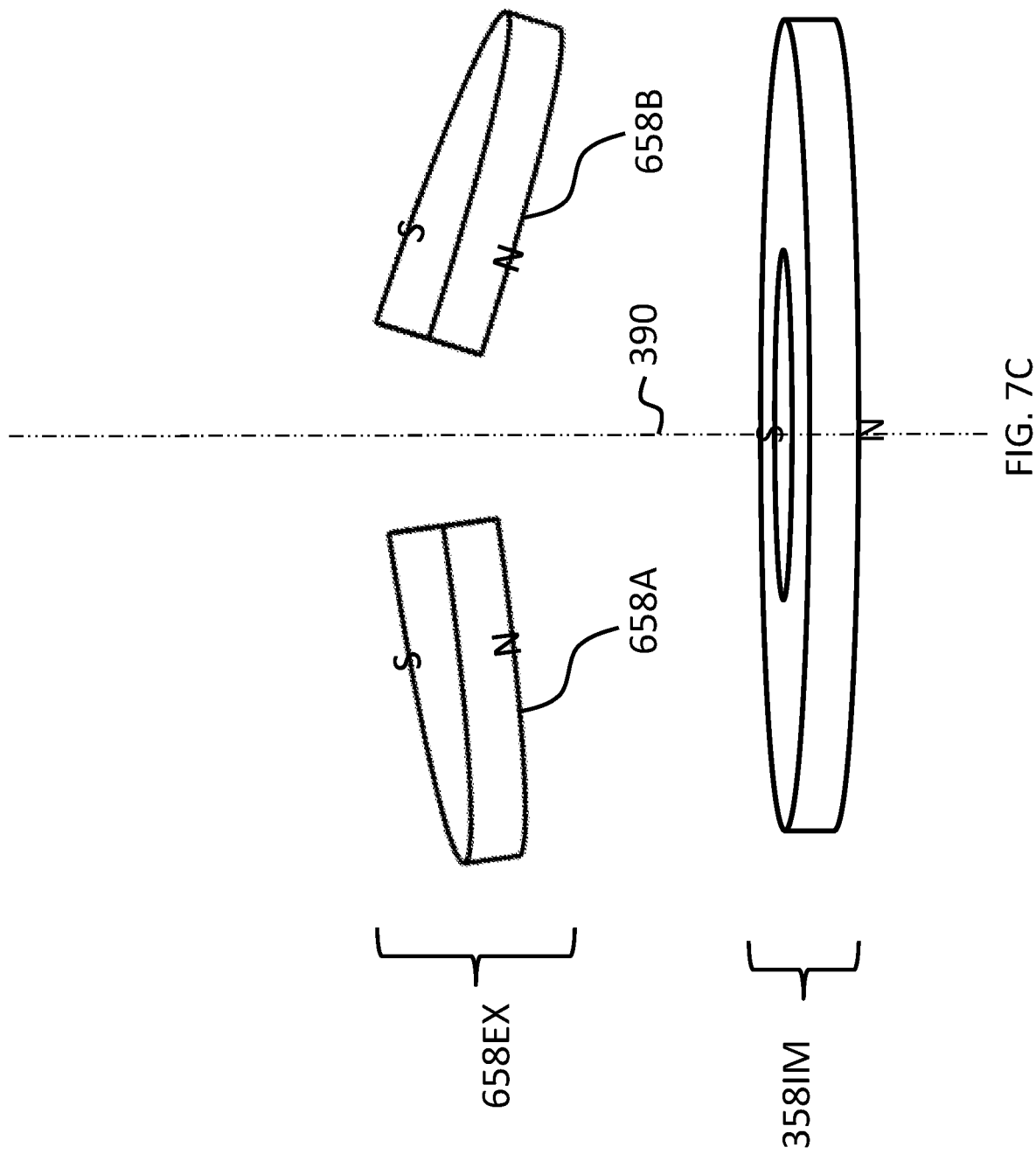

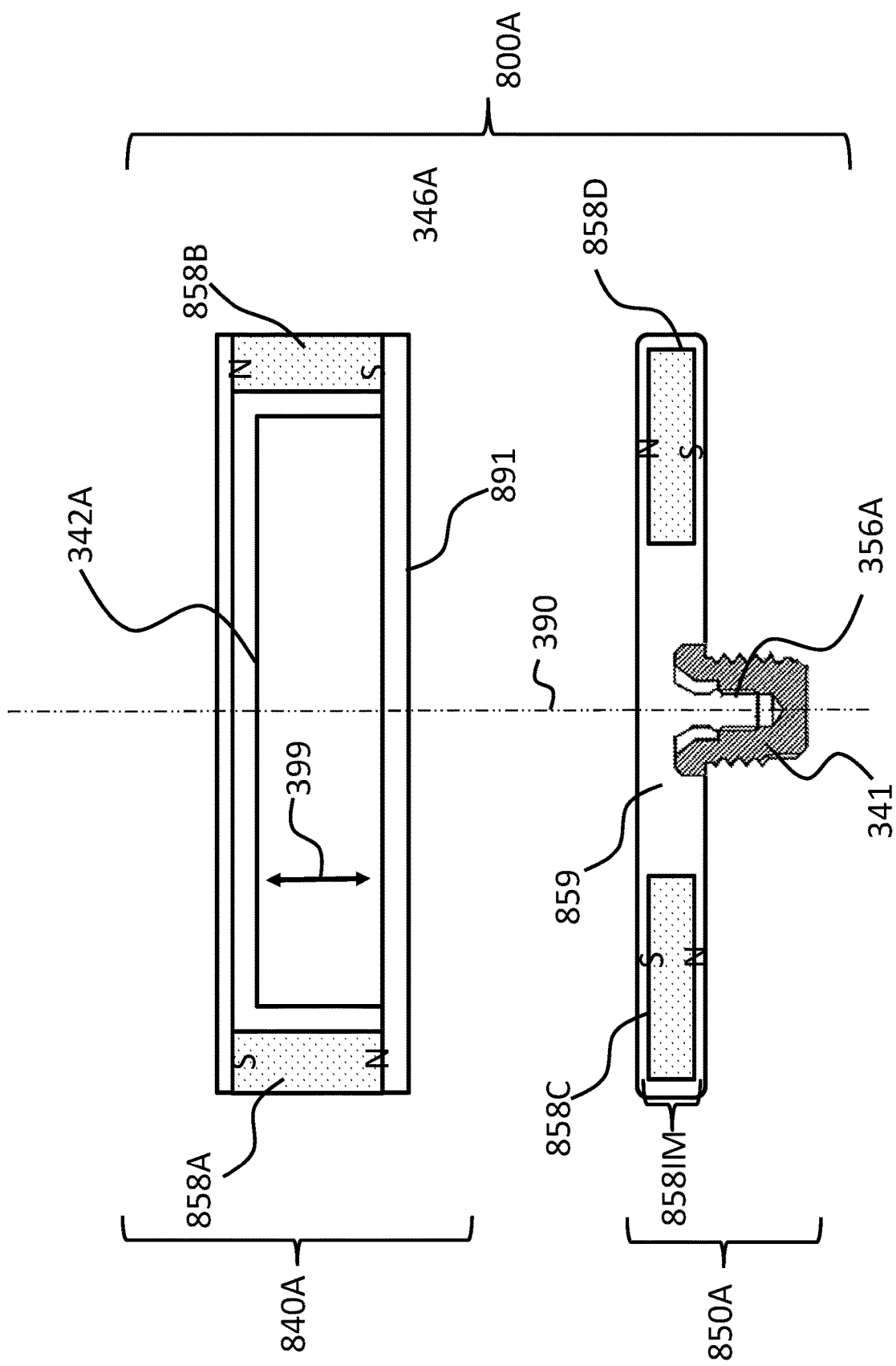

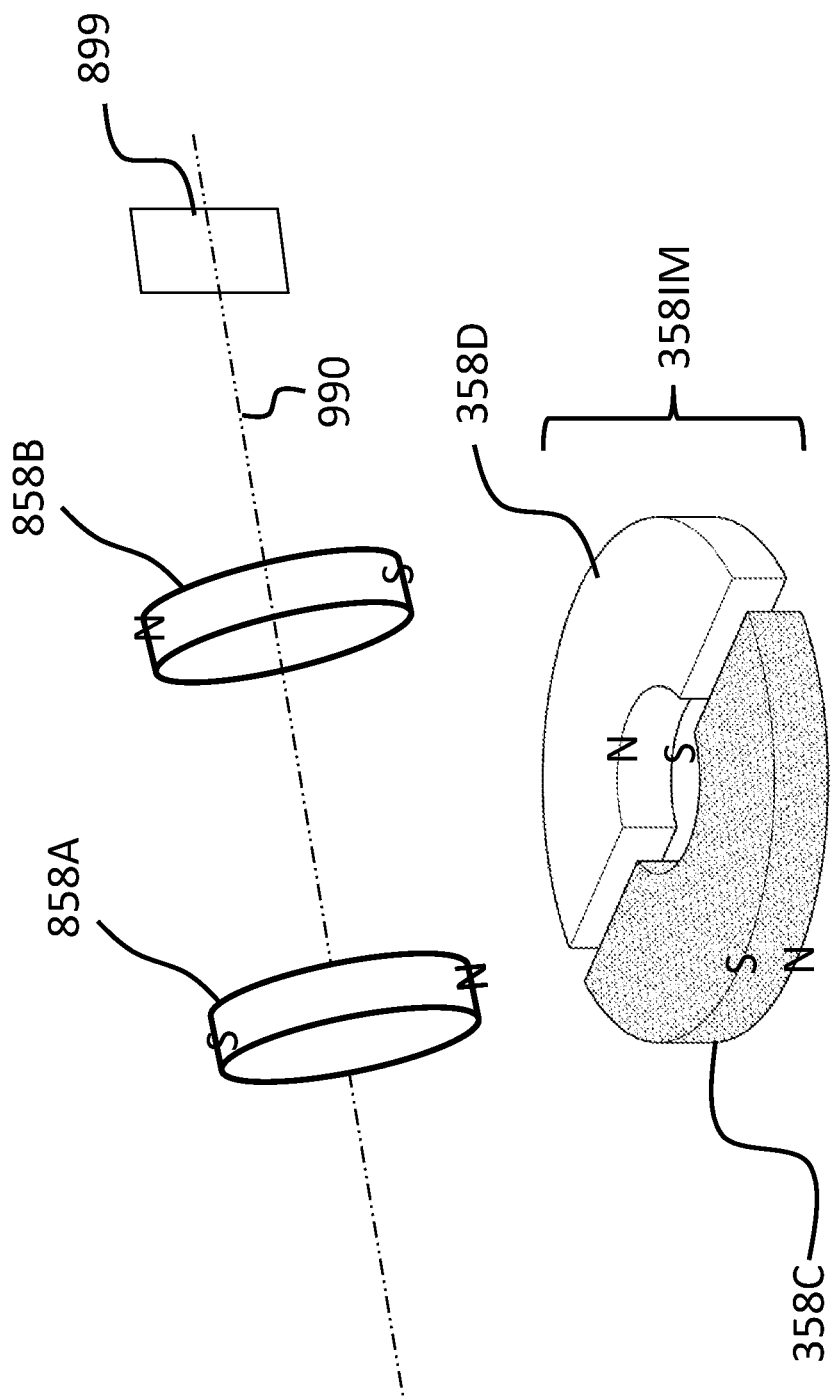

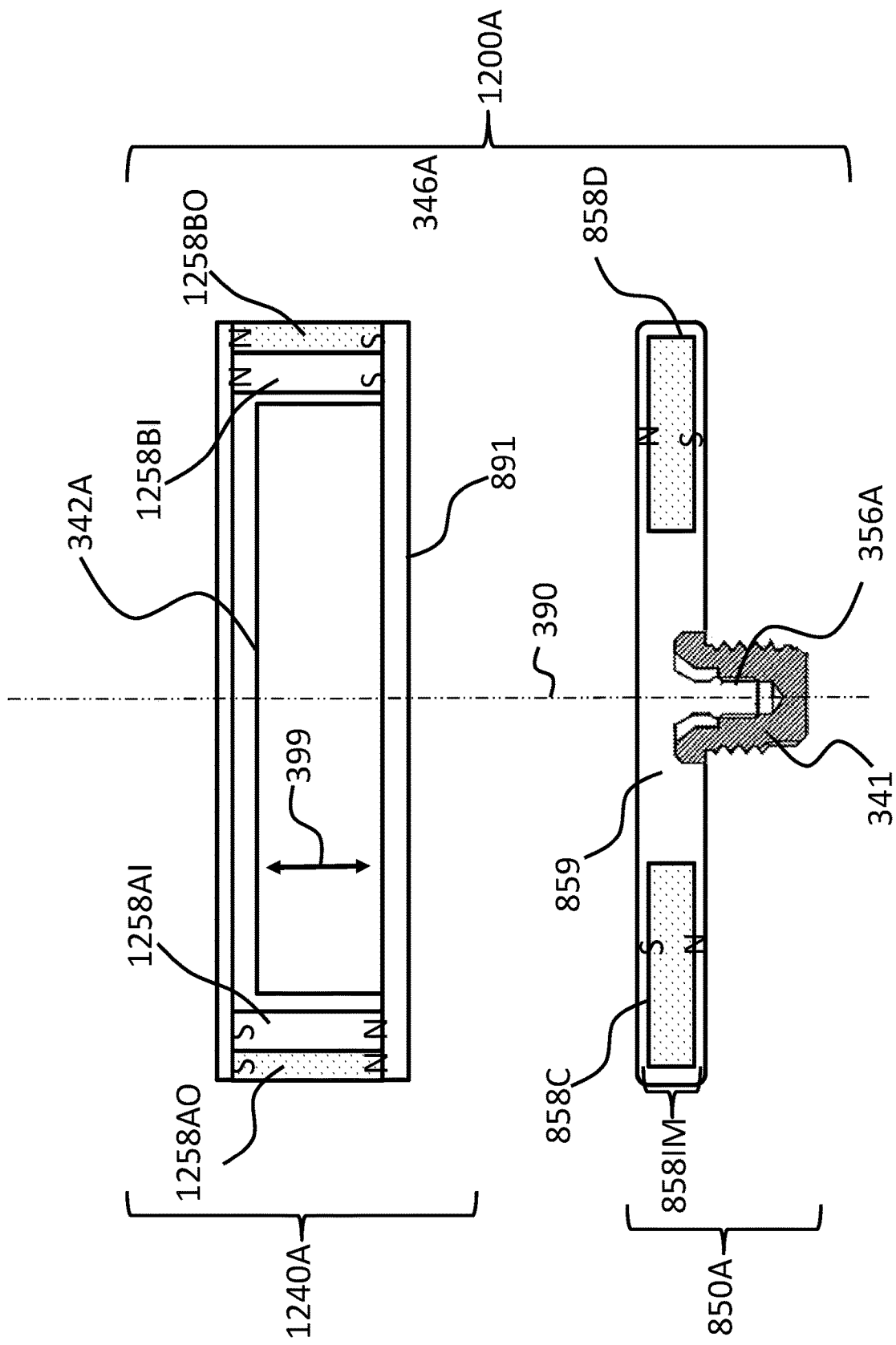

MAGNETIC RETENTION DEVICE

CROSS-REFERENCE TO RELATED APPLICATIONS

This application is a Continuation application of U.S. patent application Ser. No. 17/973,930, filed Oct. 26, 2022, which is a Continuation application of U.S. patent application Ser. No. 15/161,750, filed May 23, 2016, which claims priority to Provisional U.S. Patent Application No. 62/185,288, entitled MAGNETIC RETENTION DEVICE, filed on Jun. 26, 2015, naming Johan GUSTAFSSON of Sweden as an inventor, the entire contents of each application being incorporated herein by reference in their entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as bone conduction devices, convert a received sound into vibrations. The vibrations are transferred through the skull to the cochlea causing generation of nerve impulses, which result in the perception of the received sound. Bone conduction devices are suitable to treat a variety of types of hearing loss and may be suitable for individuals who cannot derive sufficient benefit from acoustic hearing aids, cochlear implants, etc, or for individuals who suffer from stuttering problems.

SUMMARY

In accordance with an exemplary embodiment, there is an apparatus comprising an external component of a medical device, and an implantable component of the medical device, wherein the apparatus is configured to generate a magnetic flux that removably retains, via a resulting magnetic retention force, the external component to a recipient thereof, wherein the external apparatus is configured to enable the adjustment of a path of the generated magnetic flux so as to vary the resulting magnetic retention force.

In accordance with another exemplary embodiment, there is an apparatus, comprising an external component of a medical device including a permanent magnet having a polarity axis, the external component being configured such that the permanent magnet at least partially removably retains, via a resulting magnetic retention force, the external component to a recipient thereof, wherein the external component is configured to enable the adjustment of an orientation of the polarity axis.

In accordance with another exemplary embodiment, there is a method, comprising obtaining an external component of a medical device configured to be magnetically retained against outer skin of a recipient, via a magnetic coupling between the external component and an implanted component in the recipient, and adjusting a path of a magnetic flux generated by the external component such that the resulting retention force of the magnetic retention for the recipient is varied from that which was the case prior to the adjustment.

BRIEF DESCRIPTION OF THE DRAWINGS

Some embodiments are described below with reference to the attached drawings, in which:

FIGS. 4A-4C are schematic diagrams illustrating adjustment of a component of the embodiment of FIG. 3;

FIGS. 5A-5B are schematic diagrams illustrating exemplary magnetic flux paths of the embodiment of FIG. 3;

FIG. 6 depicts another exemplary embodiment;

FIGS. 7A-7C are schematic diagrams illustrating adjustment of a component of the embodiment of FIG. 6;

FIG. 8 depicts another exemplary embodiment;

FIGS. 9A-9D are schematic diagrams illustrating adjustment of a component of the embodiment of FIG. 8;

FIG. 12 depicts another exemplary embodiment;

DETAILED DESCRIPTION

Figure 1:
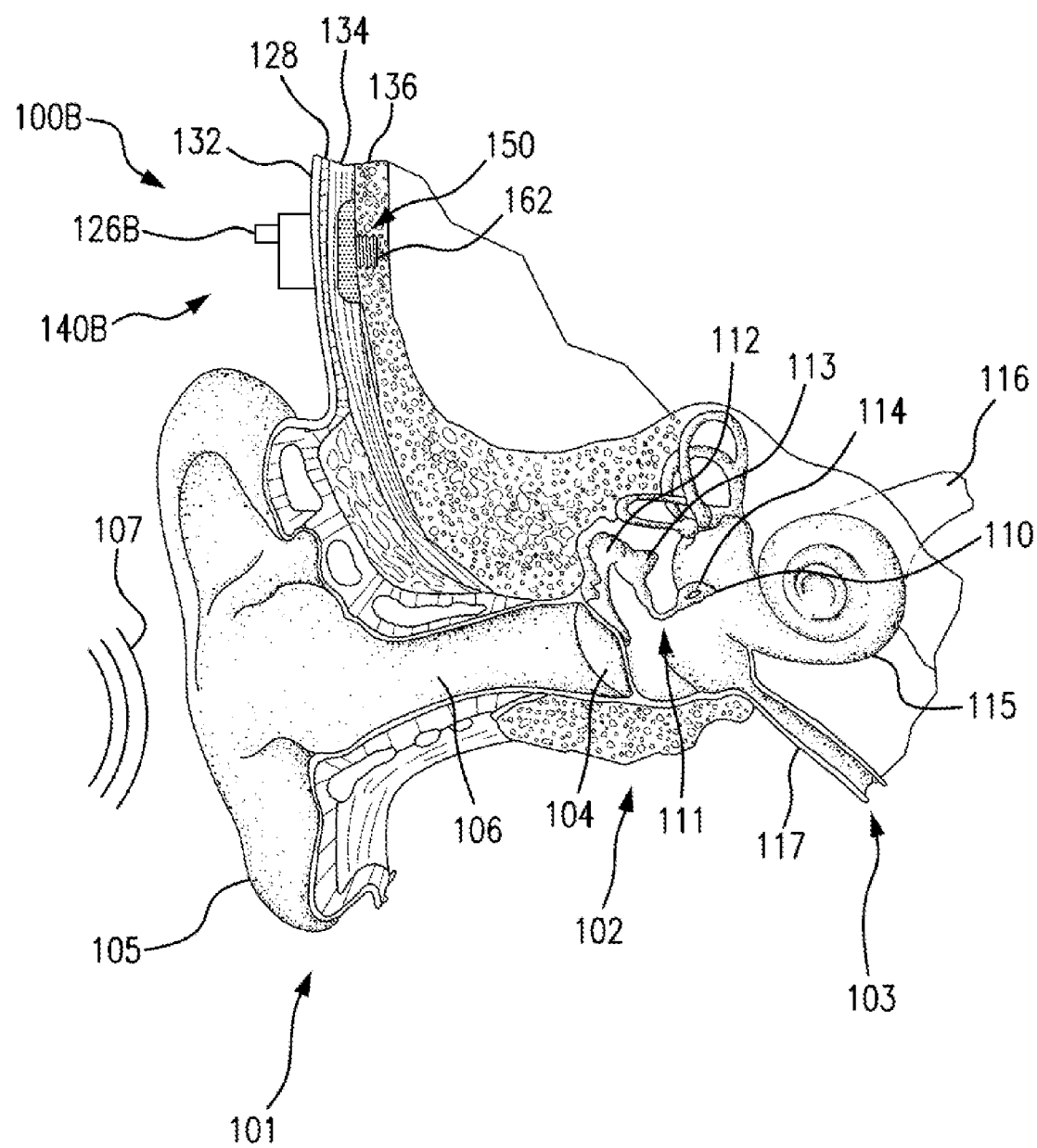
FIG. 1 is a perspective view of an exemplary bone conduction device in which at least some embodiments can be implemented.

FIG. 1 is a perspective view of a bone conduction device 100 in which embodiments may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 210 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient and comprises a sound input element 126 to receive sound signals. Sound input element may comprise, for example, a microphone, telecoil, etc. In an exemplary embodiment, sound input element 126 may be located, for example, on or in bone conduction device 100, or on a cable extending from bone conduction device 100.

The bone conduction device 100 of FIG. 1 is a passive transcutaneous bone conduction device utilizing the electromagnetic actuators disclosed herein and variations thereof where no active component (e.g., the electromagnetic actuator) is implanted beneath the skin (it is instead located in an external device), and the implantable part is, for instance a magnetic pressure plate (a permanent magnet, ferromagnetic material, etc.). Some embodiments of the passive transcutaneous bone conduction systems are configured for use where the vibrator (located in an external device) containing the electromagnetic actuator is held in place by pressing the vibrator against the skin of the recipient. In an exemplary embodiment, the vibrator is held against the skin via a magnetic coupling (magnetic material and/or magnets being implanted in the recipient and the vibrator having a magnet and/or magnetic material that used to complete the magnetic circuit, thereby coupling the vibrator to the recipient).

More specifically, FIG. 1 is a perspective view of a passive transcutaneous bone conduction device 100 in which embodiments can be implemented.

Bone conduction device 100 comprises an external component 140 and an implantable component 150. Bone conduction device 100 comprises a sound processor (not shown), an actuator (also not shown) and/or various other operational components. In operation, sound input device 126 converts received sounds into electrical signals. These electrical signals are utilized by the sound processor to generate control signals that cause the actuator to vibrate. In other words, the actuator converts the electrical signals into mechanical vibrations for delivery to the recipient's skull.

In accordance with some embodiments, a fixation system 162 may be used to secure implantable component 150 to skull 136. As described below, fixation system 162 may be a bone screw fixed to skull 136, and also attached to implantable component 150.

In one arrangement of FIG. 1, bone conduction device 100 is a passive transcutaneous bone conduction device. In such an arrangement, the active actuator is located in external component 140, and implantable component 150 includes a plate, as will be discussed in greater detail below. The plate of the implantable component 150 vibrates in response to vibration transmitted through the skin, mechanically and/or via a magnetic field, that are generated by an external magnetic plate.

Figure 2:
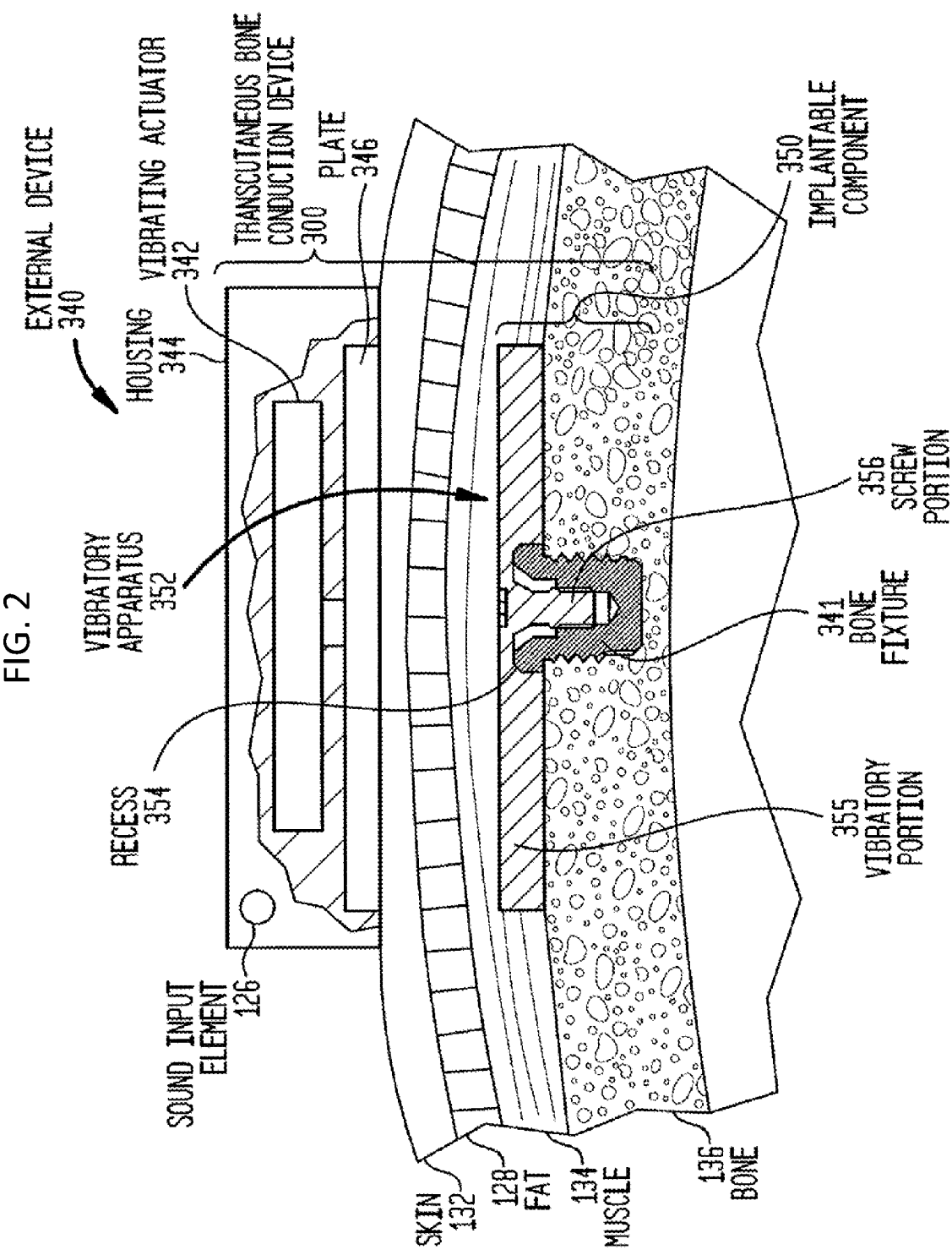
FIG. 2 is a schematic diagram conceptually illustrating a passive transcutaneous bone conduction device in accordance with at least some exemplary embodiments.
Figure 3:
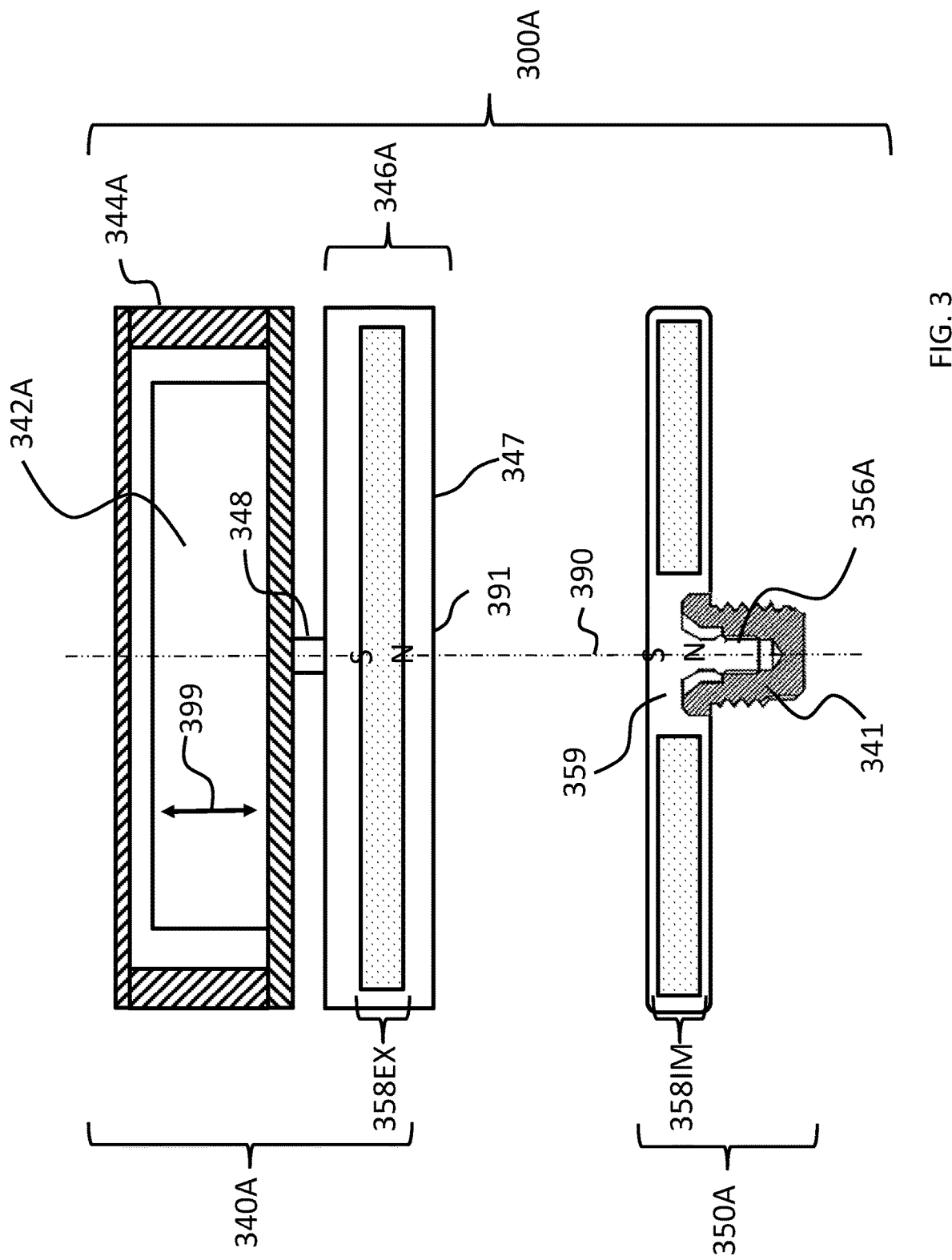
FIG. 3 is a schematic diagram illustrating additional details of the embodiment of FIG. 2.

FIG. 2 depicts a functional schematic of an exemplary embodiment of a transcutaneous bone conduction device 300 according to an embodiment that includes an external device 340 (corresponding to, for example, element 140 of FIG. 1) and an implantable component 350 (corresponding to, for example, element 150 of FIG. 1). The transcutaneous bone conduction device 300 of FIG. 3 is a passive transcutaneous bone conduction device in that a vibrating electromagnetic actuator 342 is located in the external device 340. Vibrating electromagnetic actuator 342 is located in housing 344 of the external component, and is coupled to plate 346. In an exemplary embodiment, the vibrating electromagnetic actuator 342 is a device that converts electrical signals into vibration. In operation, sound input element 126 converts sound into electrical signals. Specifically, the transcutaneous bone conduction device 300 provides these electrical signals to vibrating actuator 342, or to a sound processor (not shown) that processes the electrical signals, and then provides those processed signals to vibrating electromagnetic actuator 342. The vibrating electromagnetic actuator 342 converts the electrical signals (processed or unprocessed) into vibrations. Because vibrating electromagnetic actuator 342 is mechanically coupled to plate 346, the vibrations are transferred from the vibrating actuator 342 to plate 346. Implanted plate assembly 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient, as will be detailed further below. Accordingly, vibrations produced by the vibrating electromagnetic actuator 342 of the external device 340 are transferred from plate 346 across the skin to plate 355 of implanted plate assembly 352. This can be accomplished as a result of mechanical conduction of the vibrations through the skin, resulting from the external device 340 being in direct contact with the skin and/or from the magnetic field between the two plates. These vibrations are transferred without penetrating the skin with a solid object such as an abutment as detailed herein with respect to a percutaneous bone conduction device.

As may be seen, the implanted plate assembly 352 is substantially rigidly attached to a bone fixture 341 in this embodiment. Plate screw 356 is used to secure plate assembly 352 to bone fixture 341. The portions of plate screw 356 that interface with the bone fixture 341 substantially correspond to an abutment screw discussed in some additional detail below, thus permitting plate screw 356 to readily fit into an existing bone fixture used in a percutaneous bone conduction device. In an exemplary embodiment, plate screw 356 is configured so that the same tools and procedures that are used to install and/or remove an abutment screw (described below) from bone fixture 341 can be used to install and/or remove plate screw 356 from the bone fixture 341 (and thus the plate assembly 352).

Referring now to FIG. 3, there is depicted a schematic of an exemplary bone conduction device 300A corresponding to bone conduction device 300 of FIG. 2. The exemplary bone conduction device 300A of FIG. 3 includes an external component 340A corresponding to external component 340 of FIG. 2, and an implantable component 350A corresponding to implantable component 350 of FIG. 2.

In an exemplary embodiment, external component 340A has the functionality of a transducer/actuator, irrespective of whether it is used with implantable component 350A. That is, in some exemplary embodiments, external component 340A will vibrate whether or not the implantable component 350A is present (e.g., whether or not the static magnetic field extends to the implantable component 350A, as will be detailed below).

The external component 340A includes a vibrating actuator represented in black-box format by reference numeral 342A. In an exemplary embodiment, the vibrating actuator can be an electromagnetic actuator. Alternatively, in some alternate embodiments, the vibrating actuator 342A can be a piezoelectric actuator. Any type of an actuator that can enable the teachings detailed herein and/or variations thereof to be practiced can be utilized in at least some exemplary embodiments. That said, embodiments detailed herein will be described, by way of example only and not by way of limitation, in terms of a vibrating electromagnetic actuator that utilizes a bobbin about which is wound a coil that is energized and deenergized in an alternating manner, so as to produce an electromagnetic field that interacts with permanent magnets that move a seismic mass in a vibratory matter in a direction of arrow 399.

Still with reference to FIG. 3, the vibrating electromagnetic actuator 342A is enclosed in a housing 344A, as can be seen. In some embodiments, the housing 344A is a hermetically sealed housing, while in other embodiments, it is not hermetically sealed. In at least some exemplary embodiments, the housing 344A is configured to provide the actuator 342A protection from shock and environmental conditions, etc. Any housing that can enable the teachings detailed herein and/or variations thereof can be utilized in at least some embodiments. In this regard, as can be seen, the housing 344A is rigidly attached to skin interface portion 346A, which functionally corresponds to plate 346 of FIG. 2 detailed above, by structural component 348. In this exemplary embodiment, the structural component 348 provides a vibrational conduction path such that vibrations generated by actuator 342A are transferred from the housing to the skin interface component 346A, such that those vibrations can then be transferred into the skin of the recipient to ultimately evoke a hearing percept according to the teachings detailed herein and/or variations thereof.

In at least some embodiments, skin interface portion 346A serves a dual role in that it both transfers vibrations from the external component 340A to the skin and also magnetically couples the external component 340A to the recipient. In this regard, as can be seen, skin interface portion 346A includes a housing 347 that includes an external magnet assembly 358EX. External magnetic assembly 358EX includes a permanent magnet (as shown in FIG. 3, but in alternate embodiments, the external magnet assembly 358EX can have a plurality of magnets) having a North-South alignment (or a plurality of magnets collectively resulting in the external magnet assembly 358EX having a North-South alignment. As will be detailed in greater detail below, the external magnet assembly 358EX is tiltable relative to the longitudinal axis 390 of the external component/the housing 347/surface 391. As can be seen, the magnet assembly 358EX has a North Pole away from actuator 342A (i.e., toward the skin of the recipient). That is, the North-South alignment of the external magnet assembly 358EX is oriented towards skin of the recipient. However, in other exemplary embodiments of the external component 340A, the poles are different than that depicted in FIG. 3. In an exemplary embodiment, the permanent magnet of magnet assembly 358EX is a disk magnet.

It is noted that the word "adjustable" and "tiltable" as used herein excludes replacement of one magnet with another magnet, that being a reconfiguration or a modification to the device.

Skin interface portion 346A includes a bottom surface 391 (relative to the frame of reference of FIG. 3) that is configured to interface with the exterior skin of the recipient. In this regard, skin interface portion 346A corresponds to plate 346 of FIG. 2 as described above. It is through skin interface portion 346A that vibrations generated by the electromagnetic actuator of the external component 340A are transferred from the external component 340A to the skin of the recipient to evoke a hearing percept. In an exemplary embodiment, the housing 347 of the skin interface portion 346A is made of a non-ferromagnetic material that is compatible with skin of the recipient (or at least is coated with a material that is compatible with skin of the recipient). In this regard, in at least some exemplary embodiments, the housing 347 is configured to substantially avoid influencing the magnetic flux generated by the permanent magnet of the external magnet assembly 358EX.

FIG. 3 also depicts an implantable component 350A corresponding to implantable component 350 of FIG. 2. In some embodiments, implantable component 350 includes an implantable magnet assembly 358IM that includes single permanent magnet, such as a doughnut magnet (depicted in FIG. 3 in cross-sectional view without background structure for clarity). The permanent magnet has a North-South alignment in a first direction relative to a longitudinal axis of the electromagnetic actuator (the vertical direction of FIG. 3). In the exemplary embodiment of FIG. 3, the permanent magnet assembly has a North-South alignment with the South Pole facing the external component 340A (the surface of the skin of the recipient). That said, in an alternate embodiment, as with the external magnet assembly 358EX, the implantable magnet assembly 358IM can include a plurality of magnets that are arrayed such that the overall assembly has a polar axis as desired.

In an exemplary embodiment, the chassis 359 that supports or otherwise retains the permanent magnet(s) of the implantable magnet assembly 358IM is a nonmagnetic material (e.g., titanium). It is noted that in alternative embodiments, other configurations can be utilized. Any configuration of a permanent magnet assembly that can enable the teachings detailed herein and/or variations thereof to be practiced can be utilized in at least some embodiments.

That said, in an alternative embodiment, it is noted that the implantable component 350A does not include permanent magnet(s). In at least some embodiments, the permanent magnet is replaced with other types of ferromagnetic material (e.g., soft iron (albeit encapsulated in titanium, etc.)). In the embodiment of FIG. 3, the magnet of assembly 358IM is a single, monolithic component, but in alternate embodiments, the assembly 358IM uses multiple magnets. Any configuration of ferromagnetic material of the implantable component 350A that will enable the permanent magnets of the external component 340A to establish a magnetic coupling with the implantable component 350A that will enable the external component 340A to be adhered to the surface of the skin, as detailed herein, can be utilized in at least some embodiments.

As can be seen, implantable component 350A includes screw component 356A configured to screw into bone fixture 341 and thus secure the chassis 359 to the bone fixture 341, and thus to the recipient.

Referring back to the external component 340A, there is seen an apparatus (bone conduction device 300A), comprising an external component 340A including a permanent magnet 358EX having a polarity axis (the N-S axis, as seen). In an exemplary embodiment, the external component 340A is configured such that the permanent magnet 358EX at least partially removably retains, via a resulting magnetic retention force, the external component 340A to a recipient thereof, wherein the external component 340a is configured to enable the adjustment of an orientation of the polarity axis of the permanent magnet assembly 358EX. In an exemplary embodiment, this adjustment of the orientation of the polarity axis is achieved by tilting the permanent magnet assembly 358EX.

In an exemplary embodiment, as will be discussed in greater detailed below, the adjustments of the orientation of the polarity axis of the permanent magnet assembly 358EX enables adjustment of a path of the generated magnetic flux that is generated by the permanent magnets of the permanent magnet assembly 358EX. In an exemplary embodiment, this varies the resulting magnetic retention force between the external component 340A and the implantable component 350A, also as detailed below.

In this regard, in at least some exemplary embodiments, during operational use of the bone conduction device 300A, the external magnet assembly 358EX has a polar axis aligned with the magnets of the implantable magnet assembly 358IM such that the poles of the external magnet assembly 358EX have a North-South alignment in exactly the same direction as the implantable magnet assembly 358IM, in a scenario where maximum attractive force between the external component 340A and the implantable component 350A is desired. This is depicted in FIG. 3.

Conversely, in at least some exemplary embodiments, during operational use of the bone conduction device 300A, the external magnet assembly 358EX is tilted such that the North-South axis is misaligned with the North-South axis of the implantable magnet assembly 358IM, not because the external component 340A has been globally tilted relative to the implantable component 350A (or, alternatively, the effective reduction in force is not due to the external component 340A being globally tilted to the implantable component 350A— the external component may tilt a bit, but the effect of the tilt is relatively negligible on the variation of the retention force), but because of the adjustability of the external magnet assembly 358EX due to the tiltability feature.

Figure 4B:
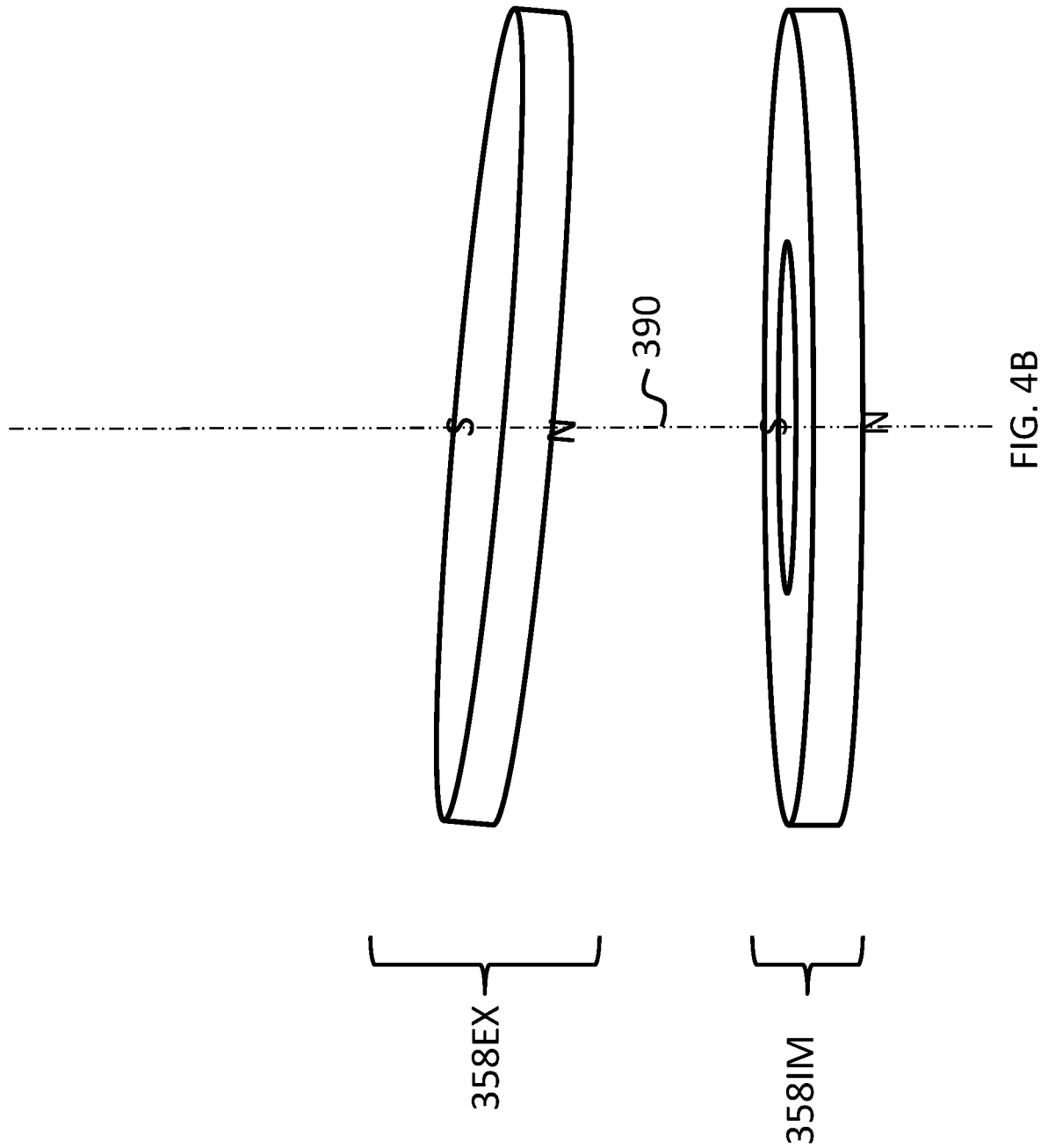

The above adjustability can be conceptually seen in FIGS. 4A-C, which conceptually depict respective isometric views of the external magnet assembly and the internal magnet assembly without any of the components of the bone conduction device 300A. More specifically, FIG. 4A depicts a configuration of the external magnet assembly 358EX such that the maximum attraction force between the external component 340A and 350A is achieved. Briefly, with respect to the frame of reference of FIGS. 4A-4C, the view of these figures corresponds to the plane of FIG. 3 except that the viewer is looking slightly from the top.

As can be seen in FIG. 4A, the magnet of the external component is a single disc shaped magnet, and the magnet of the implantable component is a single doughnut shaped magnet. As will be detailed below, other configurations can be utilized.

FIG. 4B depicts the external magnet assembly 358EX tilted by a first amount relative to the location of that assembly depicted in FIG. 4A (and thus having an angular offset relative to the longitudinal axis 390). In these embodiments, whereas the configuration of FIG. 4A results in the strongest attraction force (for a given air gap between the external magnet assembly 358EX and the implantable magnet assembly 358IM— more on this below) between the external component 340A and the implantable component 350A, the configuration of FIG. 4B results in an attraction force that is in between that FIG. 4A and FIG. 4C detailed below (again for the given air gap) between the external component 340A and the implantable component 350. FIG. 4C depicts the external magnet assembly 358EX tilted by a second amount relative to the location of that assembly depicted in FIG. 4A, where the second amount is about twice that amount of the difference between FIGS. 4A and 4B. In these embodiments, whereas the configuration of FIG. 4A results in the strongest attraction force (for a given air gap between the external magnet assembly 358EX and the implantable magnet assembly 358IM— more on this below) between the external component 340A and the implantable component 350A, the configuration of FIG. 4C results in an attraction force that is the weakest (relative to FIGS. 4A and 4B), again for the given air gap, between the external component 340A and the implantable component 350.

It is noted that the amount of tilting depicted in FIGS. 4A-4C is simply exemplary and presented for conceptual purposes. The actual amount of tilting can vary depending on the utilitarian features to be achieved. Moreover, while three different tilt amounts are depicted in the figures, respectively, some embodiments will utilize fewer or more tilt amounts. In an exemplary embodiment, the tilt amount is defined by discrete increments (e.g., a digital arrangement). By way of example only and not by way of limitation, the external component can be configured such that the external magnet assembly 358EX can set at a tilt angle of 0 degrees, 5 degrees, 10 degrees, 15 degrees, 20 degrees, 30 degrees, 40 degrees or 45 degrees. Fewer or more increments can be provided. Each setting will result in a discrete attraction force for a given airgap. Alternatively and/or in addition to this, the external component can be configured such that the external magnet assembly 358EX can be set at a tilt angle in an analogue manner. That is, the tilt angle can be set at basically any angle limited only by the fine adjustment abilities of the mechanical adjustment system (or electromechanical adjustment system, if such is used). Accordingly, in an exemplary embodiment, the tilt angle can be set at an unlimited number of different tilt angles (when the last decimal place is taken into account), limited only by the fine adjustment capabilities of the system and/or the user.

Any device, system or method that will enable the teachings detailed herein and/or variations thereof to be practiced can be utilized in at least some embodiments.

The physical phenomenon that results in the differences between the attraction force of the different configurations will now be described, followed by some exemplary embodiments of the structure of the bone conduction device implementing some such embodiments.

Figure 5A:
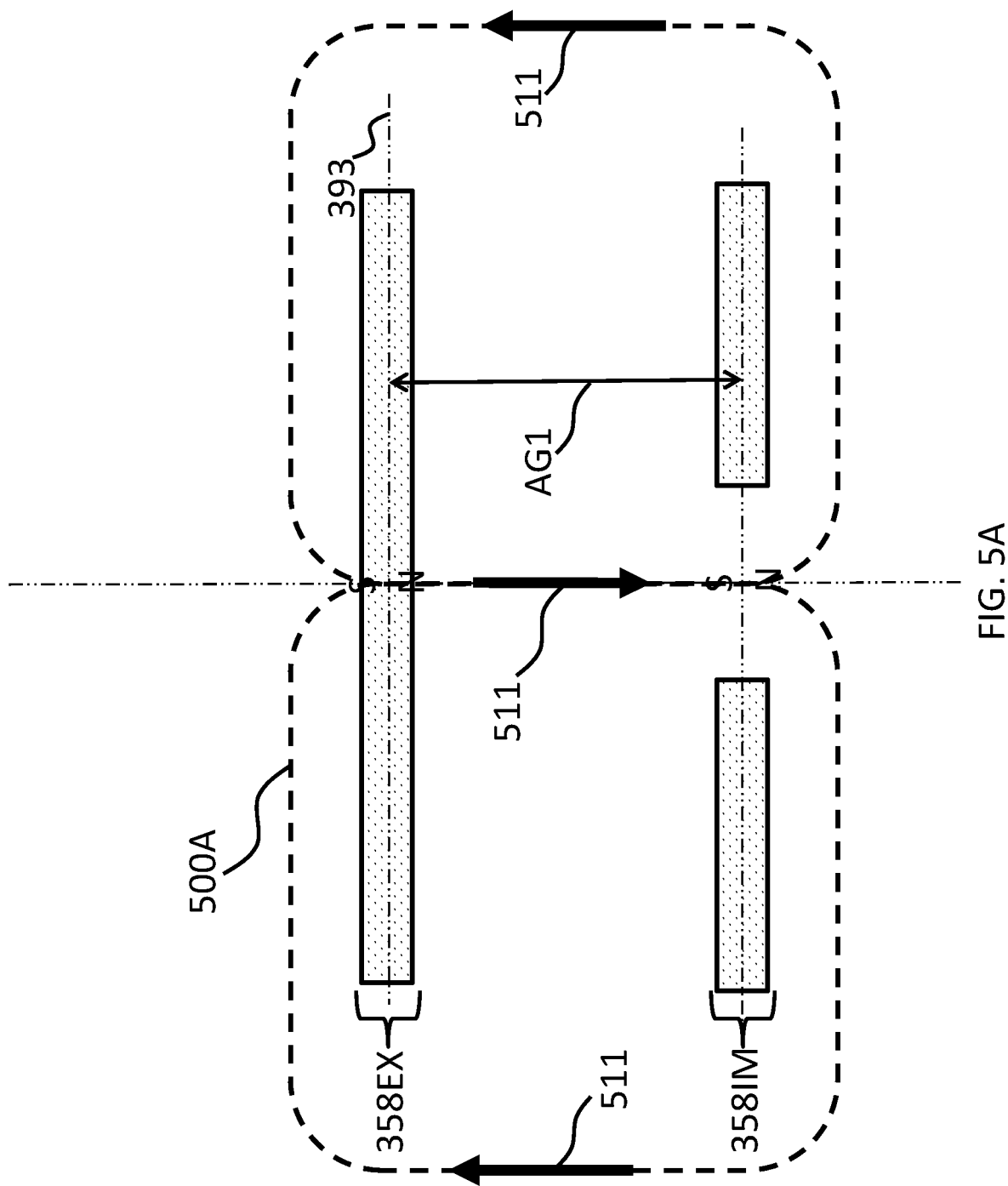

FIG. 5A depicts a quasi-functional diagram of a cross-section of the external and implantable magnet assemblies corresponding to the plane of FIG. 3 with the magnets in the arrangement as presented in FIG. 4A, with the magnetic flux following a magnetic flux path 500A. It is noted that the magnetic flux paths presented herein are presented as conceptual diagrams only to illustrate general physical phenomenon that Applicant utilizes in some embodiments. These are simplified versions of the generally more complex flux paths that occur, and are presented for purposes of illustration only. In at least some embodiments, applicants utilize the exact flux paths that would result utilize a permanent magnets as detailed herein and/or variations thereof.

FIG. 5A depicts an air gap, and is linked to the distance AG1, representing the space between the external magnet assembly 358EX and the implantable magnet assembly 358IM as measured from the center of both magnet assemblies. In this regard, it is noted that the traditional concept of air gap, which is the distance from the surfaces of the magnets facing one another, has been adjusted somewhat from its conventional use by measuring the air gap from the centerlines of the magnets. In this regard, because when the air gap is measured from the outer surfaces of the magnets, the air gap will change due to the tilting of the magnet assembly if measured at a location away from the centroid, a more stable reference is useful in terms of speaking of the air gap. That said, in an alternate embodiment, the air gap can be measured from the centroid at the outer surface of the magnet, if the magnet is configured such that the rotation axis is on the bottom surface. (The aforementioned exemplary scenario is based on the magnet assembly 358EX being rotated through the center of the magnet—the center does not move relative to the longitudinal axis.)

It is noted that the phrase "air gap" refers to locations along the magnetic flux path in which little to no material having substantial magnetic aspects is located but the magnetic flux still flows through the gap. The air gap closes the magnetic field. Accordingly, an air gap is not limited to a gap that is filled by air. Indeed, in at least some embodiments, there is always some form of solid and/or liquid matter located between the opposing faces of the external and internal magnet assemblies (skin, fat, body fluids, the material of the chassis 359, material of the housing 347, etc.).

As can be seen, in an exemplary embodiment, the magnetic flux path 500A travels in a circuit through the external magnet assembly and the implantable magnet assembly. Arrows 511 depict the relative localized strength of the magnetic flux and the direction thereof in between the magnets of the external magnet assembly 358EX and the implantable magnet assembly 358IM (the strength and direction of the magnetic flux at those local locations within the air gap AG1). With respect to the cross-sectional view of FIG. 5A, the magnetic flux travels in a circulatory fashion—downward at the center of the air gap, as is represented by arrows 511, consistent with the fact that all of the poles of the magnets are aligned, and then outwards at the bottom, and then upwards at the outside of the flux, and then inwards at the top, and then down. Alternatively, if all of the magnetic poles were reversed from that seen in the figures, the magnetic flux would be in the opposite direction. Any direction of magnetic flux that will enable the teachings detailed herein and/or variations thereof to be practiced can be utilized in at least some embodiments.

Conversely, FIG. 5B depicts a quasi-functional diagram of a cross-section of the external and implantable magnet assemblies also taken through plane of FIG. 3, with the magnets in the arrangement as presented in FIG. 4B, with the magnetic flux path 500B superimposed thereon. FIG. 5B depicts an air gap AG1, where the air gap AG1 is exactly the same distance as that of FIG. 5A in this exemplary embodiment (FIG. 5B depicting the utility of measuring the air gap AG1 from the midpoints of the magnets).

As can be seen, in an exemplary embodiment, the magnetic flux has a magnetic flux path 500B that is shifted/angled relative to which was the case in FIG. 5A. The flux path 500B is changed from 500A due to the tilting of the magnet assembly 358EX. However, owing to the fact that the implantable magnet assembly 358IM is not tilted, the shift of the magnetic flux path is not as extreme as that which would be the case in the absence of the implantable magnet assembly 358IM (or at least that which would be the case in the absence of the implantable magnet assembly 358IM having permanent magnets that also generate a magnetic flux, that is combined with that generated by the external component to generate the resulting magnetic flux 500B). (Thus, as will be understood, the external component generates a portion of the total generated magnetic flux of the bone conduction device 300A in embodiments where the implantable magnet assembly 358IM includes a permanent magnet.) This phenomenon can be seen by comparing the angle of arrow 511 to the longitudinal axis 390 of the external component 340A to the longitudinal axis 597 of the external magnet assembly 358EX (where the angle between those two axes represents the amount of tilt of the external magnet assembly 358EX relative to zero tilting). In the absence of influence of the internal magnet assembly 358IM, the arrow 511 would lie on or at least closer to axis 597, and the magnetic flux 500B would be symmetrical, or at least more symmetrical, about axis 597.

Generally speaking, the tilting of the magnetic flux path relative to that which exists at the zero tilt angle results in reduced attraction force between the external component of the implantable component, all other things being equal. In an exemplary embodiment, the more that the tilt angle increases from zero, the greater the reduction in retention force (in the micro geometry—once the magnet flips, the external component will be repelled by the implantable component—in at least some embodiments, the external component will not configured so as to enable the external magnet assembly 358EX to be flipped over). Thus, the aforementioned physical phenomenon is described in terms of the contemplated embodiments having utilitarian value with respect to retention).

Thus, an exemplary embodiment entails adjusting the orientation of the external magnet assembly 358EX and thus adjusting the orientation of the polar axis thereof to adjust a path of the generated magnetic flux generated by the external magnet assembly 358EX to vary the resulting magnetic retention force relative to that which would be the case in the absence of the tilting.

The resulting reduction in retention force is functionally represented by the fact that arrows 511 have been shortened in FIG. 5B relative to that which is the case in FIG. 5A. Accordingly, the resulting retention force holding the external component 350A against the skin of the recipient is lower than the resulting retention force of the magnetic flux of FIG. 5A.

Accordingly, in at least some exemplary embodiments, the bone conduction device 300A is configured such that the strength of the magnetic flux generated, at least in part (the implantable component can generate a portion of the magnetic flux, at least when the implantable component utilizes permanent magnets as well), by the external component can be varied for a given air gap AG1 and a given orientation of the external component 340A relative to the implantable component 350A, by adjusting the path of the generated magnetic flux. That is, by way of example only and not by way of limitation, holding all other variables constant, the magnetic flux path that retains the external component 340A to the implantable component 350A can be varied such that the resulting retention force that holds the external component 340A to the skin of the recipient is also varied by adjusting the orientation of at least one permanent magnet of the external component 340A, relative to the global geometry of the external component 340A, and thereby adjusting the resulting path. (The global geometry of the external component is represented by axis 390. By analogy, the global geometry of a car does not change even though one may adjust the locations of the seats or the steering wheel.) Unless otherwise specified, axis 390 is normal to the local direction of the skin surface at the location through which axis 390 penetrates the skin (normal to the tangent line of the skin surface at that location).

It is noted that this is different than creating additional paths for the magnetic flux to flow through, such as may result if the magnetic flux paths are short-circuited. It is also noted that this is also different than decreasing the magnetic flux density. While the former does result in new flux paths, the overall flux path remains (albeit in a weakened state). By analogy, adding additional on-ramps and off-ramps to a highway or adding additional lanes or adding a "beltway" or "express route" (that bypasses, for example, the center of a city entirely, whereas the highway sill passes through the center of the city) does not change the path of the highway). With regard to the latter, again, by way of analogy, simply decreasing the amount of traffic on a given highway by adding the bypasses or simply by limiting the number of cars permitted to utilize the highway does not change the path of the highway.

In an exemplary embodiment, the concept of changing the path of the generated magnetic flux can be defined in terms of changing the path through which the greatest amount of magnetic flux travels. In this regard, with reference to FIGS. 5A and 5B, it can be seen that the greatest amount of magnetic flux travels through the center of the magnet assemblies, and that this path has been changed.

Indeed, in an exemplary embodiment, the change in the flux path variously shortens or lengthens the overall path that the flux travels from the external component to the internal component (as opposed to changing the length of the path by adding another path that does not extend from the external component to the internal component, as can be the case in additive or subtractive flux embodiments). In this regard, again with the analogy to automobile transportation, the length of a path from Los Angeles to New York City would be lengthened if the path extended through New Orleans instead of St. Louis, but it is not a lengthened path simply because one could drive from Los Angeles to St. Louis, then to New Orleans and back to St. Louis, then to New York.

In an exemplary embodiment, a relatively longer path of the flux from the external component to the internal component reduces the attraction force between the two components relative to that which would be the case for the shorter path, and visa-versa. Again, note that all of these are for an effectively static air gap (the effective distance between the external magnet assembly and the internal magnet assembly does not substantially change (including not change)). While there may be some local movement of the external magnet assembly owing to the tilting or rotation, that movement amount has a negligible effect on the reduction in force. Also, such movement would only reduce the linear distance between the external component and the implantable component, whereas the variation of the path changes the overall trajectory of the path such that the length of the path is changed. Accordingly, in an exemplary embodiment, there is an exemplary method of varying the magnetic attractive force between the external component and the implantable component by lengthening the path of the magnetic flux between the external component and the implantable component while maintaining the air gap between the external component and the implantable component effectively constant (by effectively constant, it is meant that any change in force resulting from any change in air gap distance that might result is minor (less than 25%, less than 10%, etc.) relative to that which results from the tilting and/or rotation of the magnets).

In view of the above, in an exemplary embodiment, the aforementioned change in the length of the magnetic flux path is achieved by varying the trajectory of the magnetic flux path between the external component and the internal component.

Thus, in view of the above, an exemplary embodiment includes an external component that includes a permanent magnet that generates at least a portion of a generated magnetic flux that is used to retain the external component to the recipient. The external component is configured to enable tilting of the permanent magnet (and/or, in some alternate embodiments, rotation of the magnet, discussed in greater detail below), thereby adjusting the path of the generated magnetic flux). Concomitant with the utilitarian nature of a passive transcutaneous bone conduction device, the external component includes a skin interface surface as noted above. The action of tilting or otherwise adjusting the permanent magnet entails adjusting a longitudinal axis thereof relative to the skin interface surface. The external component is configured such that tilting of the permanent magnets so that the angle between the longitudinal axis and an axis normal to the skin interface surface is increased, decreases the resulting magnetic retention force between the external component in the implantable component. The external component is also configured such that tilting the permanent magnet so that an angle between the longitudinal axis and an axis normal to the skin interface surface is decreased, increases the resulting magnetic retention force between the external component in the implantable component.

As noted above, in at least some embodiments, rotation of the permanent magnet of the external component can be utilized to vary or otherwise adjust the path of the generated magnetic flux. In this regard, in an exemplary embodiment, the external component is configured to enable rotation of the permanent magnet.

Thus, in view of the above, in an exemplary embodiment, there is an apparatus, comprising an external component of a medical device, such as, by way of example only and not by way of limitation, external component 340 of FIG. 3, and an implantable component of a medical device, such as the implantable component 350 of FIG. 3, configured to generate a magnetic flux (e.g., via permanent magnets, which generation is thus passive) that removably retains, via a resulting magnetic retention force, the external component (e.g., 340A) to the recipient thereof. In this exemplary embodiment, the external component is configured to enable the adjustment of the path of the generated magnetic flux so as to vary the resulting magnetic retention force (as will be detailed below, in an alternate embodiment, the implantable component or both the external component and the implantable component are configured to vary the generated magnetic flux path). In this regard, as seen from the above, at least some exemplary embodiments accomplish this by tilting the permanent magnets (although in an alternative embodiment, as will be detailed below, some exemplary embodiments accomplish this by rotating the permanent magnet, such that the magnetic polar axis orientation is changed). Corollary to this is that in at least some exemplary embodiments, the external component is configured to enable the adjustment of the path of the generated magnetic flux without varying a total magnetic density of permanent magnets of the external component generating the magnetic flux.

Still further, in an exemplary embodiment of this exemplary embodiment, the external component is configured to enable the adjustment of the path of the generated magnetic flux without at least one of additive or subtractive interaction of local magnetic flux (e.g., by creating and/or varying the short-circuit in the magnetic flux, by, for example, altering/adjusting the relative locations of one or more of the permanent magnets that generate the magnetic flux).

That said, in an alternate embodiment, the external component is further configured to enable adjustment of the generated magnetic flux to vary the resulting retention force via at least one of additive or subtractive interaction of local magnetic flux.

An alternate embodiment where the external component utilizes a plurality of permanent magnets will now be described.

Referring now to FIG. 6, there is depicted a schematic of an exemplary bone conduction device 600A corresponding to bone conduction device 300 of FIG. 2. The exemplary bone conduction device 600A of FIG. 6 includes an external component 640A corresponding to external component 340 of FIG. 2, and an implantable component 350A corresponding to implantable component 350 of FIG. 2 (and that of FIG. 3).

In an exemplary embodiment, external component 640A has the functionality as detailed above with respect to external component 340A, and is identical thereto, save for the fact that it utilizes a plurality of magnets in the external permanent magnet assembly, as will now be described. In this regard, as can be seen, skin interface portion 346A includes a housing 347 that includes an external magnet assembly 658EX. External magnetic assembly 658EX includes permanent magnets having a North-South alignment. These magnets are tiltable relative to one another and relative to the global geometry of the external component, as will be detailed below. In the configuration depicted in FIG. 6 (without tilting, as will be detailed below), the magnets of the magnetic assembly 658EX, relative to the longitudinal axis 390 of the bone conduction device 300A, all have North Poles facing away from the actuator 342A (i.e., towards the skin of the recipient). However, exemplary embodiments of the external component 640A are configured such that the polarities opposite that is the figure.

The implantable component 350A is identical to that detailed above with respect to FIG. 3. In this regard, a single permanent magnet of the doughnut shape is utilized. That said, in an alternative embodiment, a plurality of magnets are utilized as well, as will be detailed below with respect to an alternate embodiment.

Again, it is noted that in an alternative embodiment, it is noted that the implantable component 350A does not include permanent magnets. In at least some embodiments, the permanent magnet thereof can be replaced with other types of ferromagnetic material (e.g., soft iron (albeit encapsulated in titanium, etc.)). Also, the implantable magnet assembly 358IM can include separate magnets (i.e., the magnet assembly 358IM is not a single, monolithic component). Any configuration of ferromagnetic material of the implantable component 350A that will enable the permanent magnets of the external component 340A to establish a magnetic coupling with the implantable component 350A that will enable the external component 340A to be adhered to the surface of the skin, as detailed herein, can be utilized in at least some embodiments.

Referring back to the external component 640A, and, more particularly, to the external magnetic assembly 658EX of the skin interface portion 346A, it can be seen that the external magnetic assembly 658EX comprises two different magnets arrayed about the longitudinal axis 390. There is permanent magnet 658A and permanent magnet 658B. As will be seen below, the permanent magnets of the external component 640A are half circle type magnets.

During operational use of the bone conduction device 600A, the magnets of the external magnet assembly 658EX are aligned with the magnets of the implantable magnet assembly 358IM, such that the poles of the permanent magnets 658A and 658B have a North-South alignment in exactly the same direction and the poles of the permanent magnet of permanent magnet assembly 358IM, in a scenario where maximum attractive force between the external component 640A and the implantable component 350A is desired. Conversely, in at least some exemplary embodiments, during operational use of the bone conduction device 600A, the magnets of the external magnet assembly 658EX are tilted in a controlled manner such that their polarity axes are non-aligned with the axes of magnets of the implantable magnet assembly 658IM, not because the external component 640A has been tilted relative to the implantable component 350A (or, alternatively, not entirely because the external component 640A has been rotated relative to the implantable component 350A), but because of the adjustability of the relative position of the magnets 658A and/or 658B.

The above tiltability can be conceptually seen in FIGS. 7A and 7B, which conceptually depict respective isometric views of the external magnet assembly and the internal magnet assembly, without any of the components of the bone conduction device 300A. More specifically, FIG. 7A depicts a configuration of the external magnet assembly 658EX such that the maximum attraction force between the external component 640A and 350A is achieved.

As can be seen in FIG. 7A, the magnets of the external component are segmented into 2 half-circle shaped magnets of approximately equal area. In embodiments corresponding to FIGS. 7A-7B, the external component 640A is configured such that the magnets thereof can be moved to have a different angular configuration relative to that depicted in FIG. 7A. Accordingly, FIG. 7B depicts the magnets of external magnet assembly 658EX tilted relative to the location of those magnets depicted in FIG. 7A. It is noted that the arrangement of FIG. 7A depicts two (2) magnets in the external component (aside from any magnets that may be present in, for example, the transducer). As will be detailed below, an alternative embodiment includes more than 2 magnets. Any number of the magnets that can enable the teachings detailed herein and/or variations thereof to be practiced can be utilized in at least some exemplary embodiments.

It is noted that while the embodiment of FIG. 7B depicts the permanent magnets of the external assembly 658EX being tilted by the same amount (albeit in opposite directions relative to the longitudinal axis 390), in alternative embodiment, the extra component 640A is configured such that the angle of tilted can be very between the two permanent magnets, as can be seen in FIG. 7C.

The end result of the embodiment of FIGS. 6-7C is that the tilting of the magnets can vary the path of the resulting magnetic flux/field, so as to vary the retention force between the external component the implantable component. The conceptual magnetic flux paths will not be described in detail, as the person of ordinary skill in the art would understand, at least through experimentation, the various paths that the magnetic flux is would take based on the varying angle of the magnets.

Accordingly, in an exemplary embodiment, the external component includes a first and second permanent magnet having respective polarity axes. The external component is configured such that the first and second permanent magnets contribute to the resulting magnetic retention force so as to at least partially removably retain, via the resulting magnetic retention force, the external component to a recipient thereof. The external component is configured to enable the adjustment of an orientation of the second polarity axis, and thereby adjust the path of the magnetic fluxes that is generated by the first and second magnets of the external component.

It is noted that in an exemplary embodiment, the external component 640A is configured such that there exists a mechanical adjustment apparatus that simultaneously adjusts the respective orientations of the first and second permanent magnets so that the first and second poles have equal and opposite adjustments relative to a longitudinal axis of the external component. By way of example only and not limitation, in an exemplary embodiment, this is achieved by a gear mechanism, or by a cam mechanism, or by a rotary actuator, or a geared linear actuator, etc. Any device, system, and/or method that can enable tilting of the magnet in synchronization can be utilized in at least some embodiments. It is further noted that any of the aforementioned arrangements can be utilized with respect to the single permanent magnet arrangement of FIG. 3, providing that such can have utilitarian value.

In this regard, by way of example, in some exemplary embodiments, the external component is a wearable medical device comprising a housing with a skin interface (e.g., formed by a platform of rigid material, such as PEEK, or by a soft pad material, such as a closed-cell foam) and a magnet that forms a transcutaneous magnetic circuit with an implanted component to secure the medical device to a recipient. The medical device of these exemplary embodiments has an adjustable yoke that mounts the magnet to the housing and a mechanical drive assembly that moves the yoke to rotate or otherwise move a polarity axis of the magnet relative to the skin interface of the housing. The mechanical drive assembly is capable of moving of the yoke from a first position, where the polarity axis of the magnet is generally normal to the skin interface, to a second position, where the polarity axis is offset from the skin interface. This facilitates adjustment of the magnetic retention force securing the wearable medical device to a recipient via modification of the transcutaneous magnetic circuit formed with the implantable component. In some embodiments, the yoke of these embodiments is adjustable to change the trajectory of a magnetic flux path that defines the transcutaneous magnetic circuit. The magnetic flux path is shortest in the first position when the polarity axis of the magnet is generally normal to the skin interface. Movement of the yoke from the first position to the second position lengthens the flux path (or visa-versa). This reduces the magnetic retention force securing the wearable medical device to the recipient. The medical device can also comprise a plurality of magnets that that are adjustable via a compound yoke assembly or separate yokes with individual drive assemblies.

The above embodiments have concentrated on utilizing tilting to vary the polar axis of the permanent magnet(s) to vary the path of the resulting magnetic flux. Some exemplary embodiments that utilize rotation will now be described. It is noted that in some embodiments, both rotation and tilting can be utilized to vary the polar axis of the permanent magnet, and thus vary the path of the resulting magnetic flux.

It is noted that while the embodiment detailed above utilize an external magnet assembly that is movable and an implantable magnet assembly that is immovable (after implantation), in an alternate embodiment, the external magnet assembly is fixed (relative to the global geometry of the external component) and the implantable magnet assembly is configured to move (relative to the global geometry of the implantable component) according to one or more or all of the movement capabilities of the external magnet assembly detailed herein (or others—again, the movements of the external magnet assembly are not limited to those detailed herein providing that the flux path can be varied in accordance with the teachings detailed herein) so as to vary the path of the magnetic flux. In an exemplary embodiment, any movement regime of the external magnet assembly is applicable to the internal magnet assembly provided that such varies the path of the magnetic flux. Still further, in an exemplary embodiment, both the external component and the implantable component are configured such that their respective magnet assemblies move relative to the global structure thereof, providing that such varies the path of the magnetic flux such that the utilitarian teachings associated therewith as detailed herein result.

Referring now to FIG. 8 there is an alternate embodiment. Briefly, this embodiment utilizes a dual pole system, where the implantable component includes two separate permanent magnets. This will be described in detail below. It is noted however, that just as the embodiments detailed above can be practiced utilizing an implantable component having two or more separate permanent magnets, the embodiments below can be utilized with an implantable components having only one permanent magnet.

FIG. 8 depicts a schematic of an exemplary bone conduction device 800A corresponding to bone conduction device 300 of FIG. 2. The exemplary bone conduction device 800A of FIG. 8 includes an external component 840A corresponding to external component 340 of FIG. 2, and an implantable component 850A corresponding to implantable component 350 of FIG. 2.

Figure 9B:

The external component 840A is somewhat different than those detailed above beyond simple fact that the type of permanent magnets used therein are different. Briefly, the permanent magnets that generate, at least in part, the magnetic flux that is utilized to retain the external component 840A to the recipient are located to the sides of transducer 342A, as opposed to between the transducer 342A and the skin of the recipient/skin interface surface 891 of the external component 840A. In an exemplary embodiment of this exemplary embodiment, at least some of the magnets are rotated in a plane parallel with the axis of the attraction force, to vary the attraction force. Instead of the external component 840A being configured such that at least some of the magnets tilt relative to the longitudinal axis 390 of the bone conduction device 800A, at least some of the magnets are adjustable/rotatable about an axis (990 as seen in FIGS. 9A-9B, discussed below) that is perpendicular to the longitudinal axis 390 and extends through the magnets of the external magnet assembly of the external component. That is, instead of the magnets being tiltable relative to the external component 840A of the bone conduction device, the magnets are adjustable locally (the magnets basically occupy the exact same space within the external component 840A, but their orientation in that space can be changed).

That said, it is noted that other embodiments can utilize both tilting and rotation to change the orientation of the polar axis of at least some magnets. Any movement or adjustment of the location of magnets that will enable the teachings detailed herein and/or variations thereof to be practiced can be utilized in at least some embodiments.

In an exemplary embodiment, external component 840A has the functionality of a transducer/actuator, irrespective of whether it is used with implantable component 850A. The external component 840A includes a vibrating actuator represented in black-box format by reference numeral 342A. Any type of actuator that can enable the teachings detailed herein and/or variations thereof to be practiced can be utilized in at least some exemplary embodiments.

External component 840A includes an external magnet assembly that includes permanent magnets having a North-South alignment. These magnets are rotationally adjustable relative to the position of the respective pole axes, as will be detailed below. However, in the configuration depicted in FIG. 8 (without adjustment as will be detailed below), the magnet on one side of the magnetic assembly, relative to the longitudinal axis 390 of the bone conduction device 800A, has the North pole facing away from the skin of the recipient, and the magnet on the other side of the magnetic assembly relative to longitudinal axis 390 of the bone conduction device all have North poles facing towards the skin of the recipient. That is, the North-South alignment of one side of the external magnet assembly is opposite that of the other side of the assembly. However, exemplary embodiments of the external component 840A are configured such that the individual magnets can be moved so that the poles are different than that depicted in FIG. 8.

The external component 840A includes a bottom surface 891 relative to the frame of reference of FIG. 3) that is configured to interface with the exterior skin of the recipient. In this regard, the bottom of the external component 840A corresponds to plate 346 of FIG. 2 as described above. It is through surface 891 that vibrations generated by the electromagnetic actuator of the external component 840A are transferred from the external component 340A to the skin of the recipient to evoke a hearing percept.

The external magnet assembly of external component 840A comprises two (2) different magnets, each arrayed on opposite sides of the longitudinal axis 390. (It is noted that in alternative embodiments, more magnets can be used, as will be detailed below). This is also the case with respect to the embodiments detailed above and any other embodiment, providing that the teachings detailed herein and/or variations thereof can be practiced.) As can be seen, there is a magnet 858A and a magnet 858B (these are circular disk magnets—more on this below). As will be detailed more thoroughly below, one or both of the permanent magnets are configured to rotate so as to vary the path of the magnetic flux generated by the external magnet assembly as a result of adjustment of the alignment of the polar axes. In this regard, in at least some exemplary embodiments, during operational use of the bone conduction device 800A, the magnets of the external magnet assembly are aligned with the magnets of the implantable magnet assembly such that the poles of the permanent magnets 858A, 858C have a North-South alignment in exactly the same direction and the poles of the permanent magnets 858B, 858D have a North-South alignment in the same direction (but opposite of that of magnets 858A and 858C) in a scenario where maximum attractive force between the external component 840A and the implantable component 350A is desired. Conversely, in at least some exemplary embodiments, during operational use of the bone conduction device 800A, the magnets of the external magnet assembly are aligned with the magnets of the implantable magnet assembly such that the poles of the permanent magnet 858A are aligned in a different direction than that of magnet 858C due to the adjustability of the relative position of the magnets 858A. Furthermore, in this exemplary embodiment, during operational use of the bone conduction device 800A, the magnets of the external magnet assembly are aligned with the magnets of the implantable magnet assembly such that the poles of the permanent magnets 858B are aligned in a different direction than that of magnet 358D because of the adjustability of the relative position of the magnet 858B. (It is also noted that the above North-South pole arrangement can be utilized for the tilting magnet assembly of FIG. 6, where the implantable component is a dual pole system.

The above adjustability can be conceptually seen in FIG. 9A-B, which conceptually depicts isometric views of the magnets 858A and 858B of the bone conduction device 800A at various orientations relative to one another. More specifically, FIG. 9A depicts a configuration of the magnets of the external magnet assembly and the implantable magnet assembly such that the maximum attraction force between the external component 840A and 350A is achieved. Briefly, with respect to the frame of reference of FIG. 9A, the plane 899 corresponds to the plane of FIG. 8, wherein the plane 899 lies on the longitudinal axis 390 of the bone conduction device 800A.

As can be seen in FIG. 9A, the magnets of the external component are segmented into 2 magnets, both of which are disk shaped. Briefly, it is noted that in at least some embodiments, the configurations of magnets 858A and 858B can be different (box shaped, bar magnets, etc. —any arrangement that can enable the teachings detailed herein and/or variations thereof to be practiced can be utilized).

In embodiments corresponding to FIGS. 9A-9B, the external component 840A is configured such that one or more of the magnets 858A and 858B can be moved to have a different angular configuration with respect to the pole alignment. Accordingly, FIG. 9B depicts the magnets shifted by an angle of about 30 degrees (magnet 858B being rotated about axis 990 in the direction of arrow 9B relative to the location of that magnet depicted in FIG. 9A, and magnet 858A being rotated about axis 990 in the direction of arrow 9A relative to the location of the magnet depicted in FIG. 9A. Thus, these magnets have an angular offset of 30 degrees relative to the positions they were in as depicted in FIG. 9A.

It is noted that in an alternate embodiment, the magnets are rotated in the same direction about axis 990. It is further noted that while the embodiments depicted in the figures herein are depicted as having rotations that are of the same amount, in an alternate embodiment, the angular rotation can be different for one or more magnets relative to one or more other magnets (either in the same direction or the alternate direction).

Figure 9C:
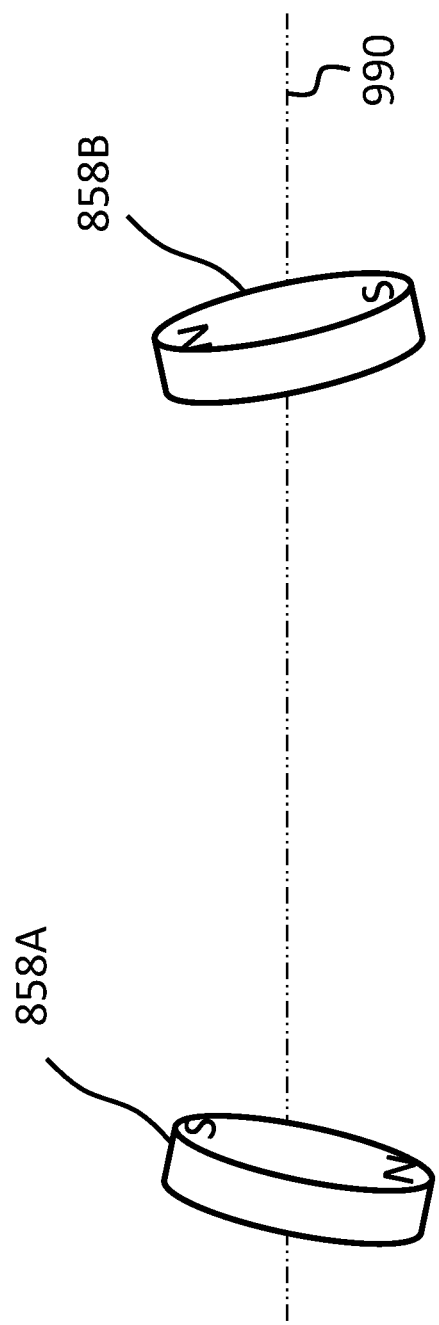
Figure 9D:
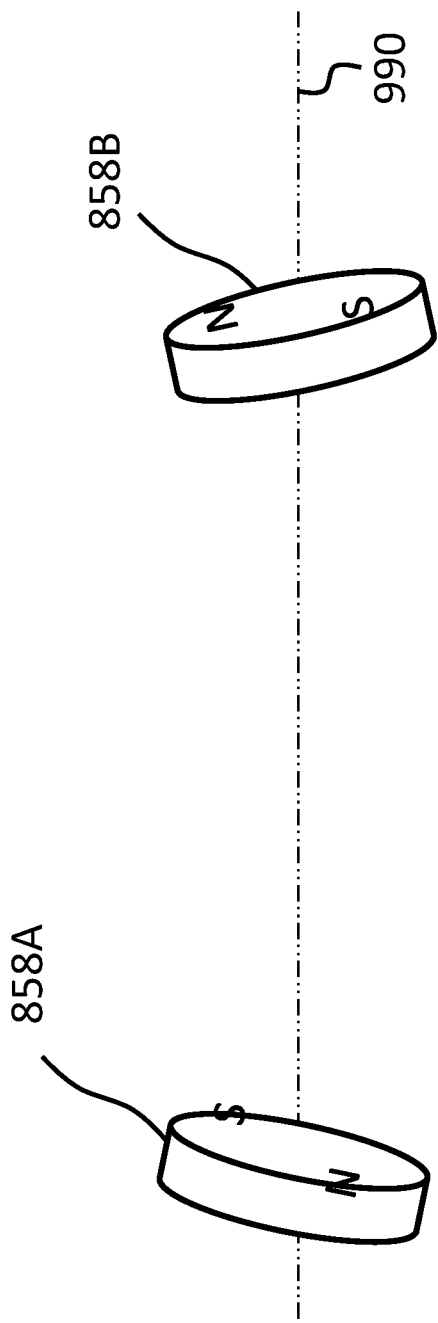

FIG. 9C depicts an alternate embodiment where the magnets 858A and 858B are tiltable, and FIG. 9D depicts an alternate embodiment where the magnets are both tiltable and rotatable. In both embodiments, the tilting and rotation vary the path of the resulting magnetic flux.

Figure 10:
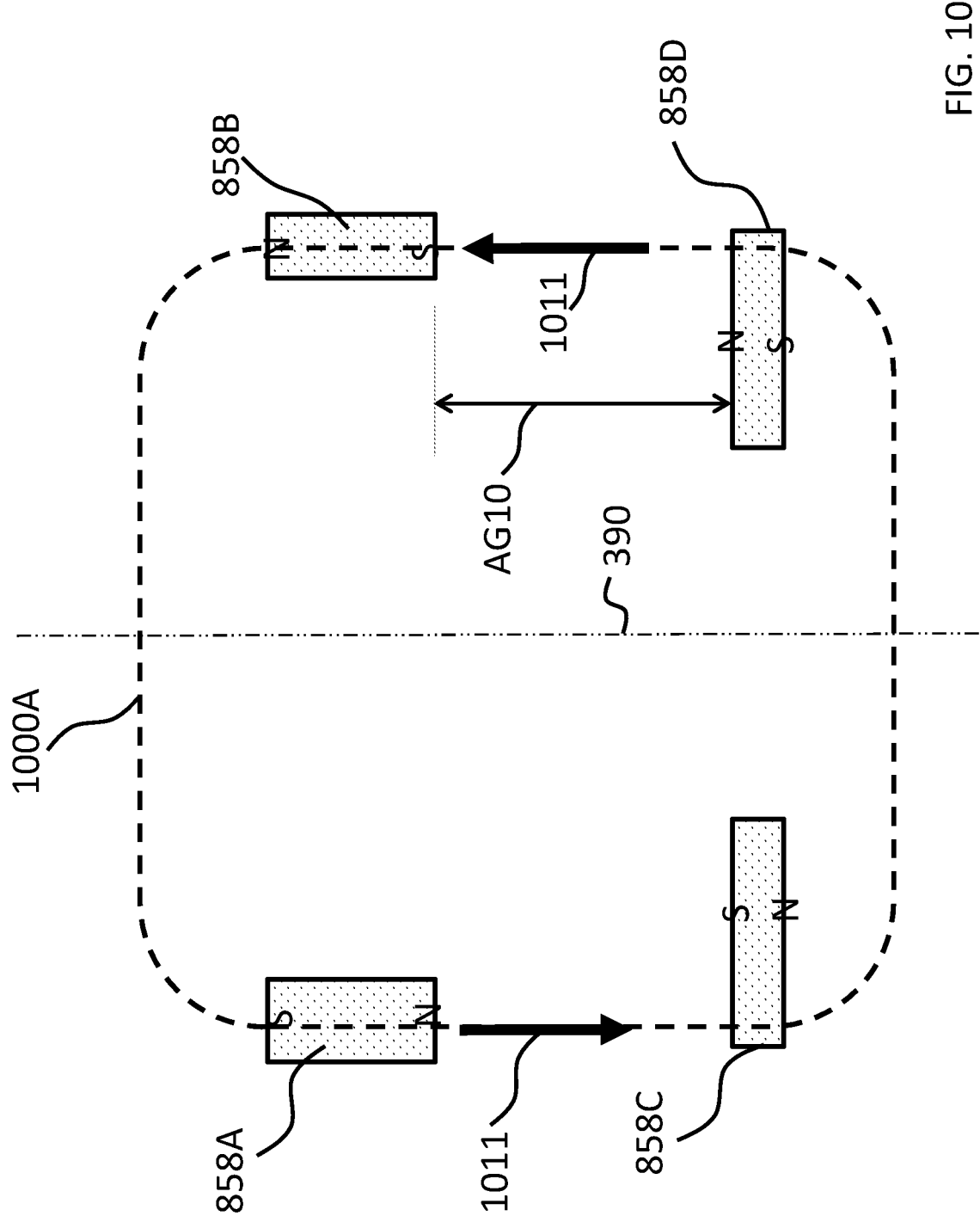
FIG. 10 is a schematic diagram illustrating exemplary magnetic flux path of the embodiment of FIG. 8.

FIG. 10 depicts a quasi-functional diagram of a cross-section of the external and implantable magnet assemblies taken through the plane of FIG. 8 with the magnets in the arrangement as presented in FIG. 9A, with the magnetic flux following a magnetic flux path 1000A. FIG. 10 depicts an air gap AG10, representing the space between the external magnet assembly 858EX and the implantable magnet assembly 858IM.

As can be seen, in an exemplary embodiment, the magnetic flux path 1000A travels in a circuit through all of the magnets of the external magnet assembly and the implantable magnet assembly. Arrows 1011 depict the relative localized strength of the magnetic flux and the direction thereof in between the magnets of the external magnet assembly 858EX and the implantable magnet assembly 858IM (the strength and direction of the magnetic flux at those local locations within the air gap AG10). With respect to the cross-sectional view of FIG. 10, the magnetic flux travels in a counterclockwise direction, as is represented by arrows 1011, consistent with the fact that all of the poles of the magnets are aligned. That said, if the view of FIG. 10 was presented from the opposite side of the longitudinal axis 390, the direction of the magnetic flux would be clockwise. Alternatively, if all of the magnetic poles were reversed from that seen in the figures, the magnetic flux would be in the opposite direction. Any direction of magnetic flux that will enable the teachings detailed herein and/or variations thereof to be practiced can be utilized in at least some embodiments.

Figure 11A:
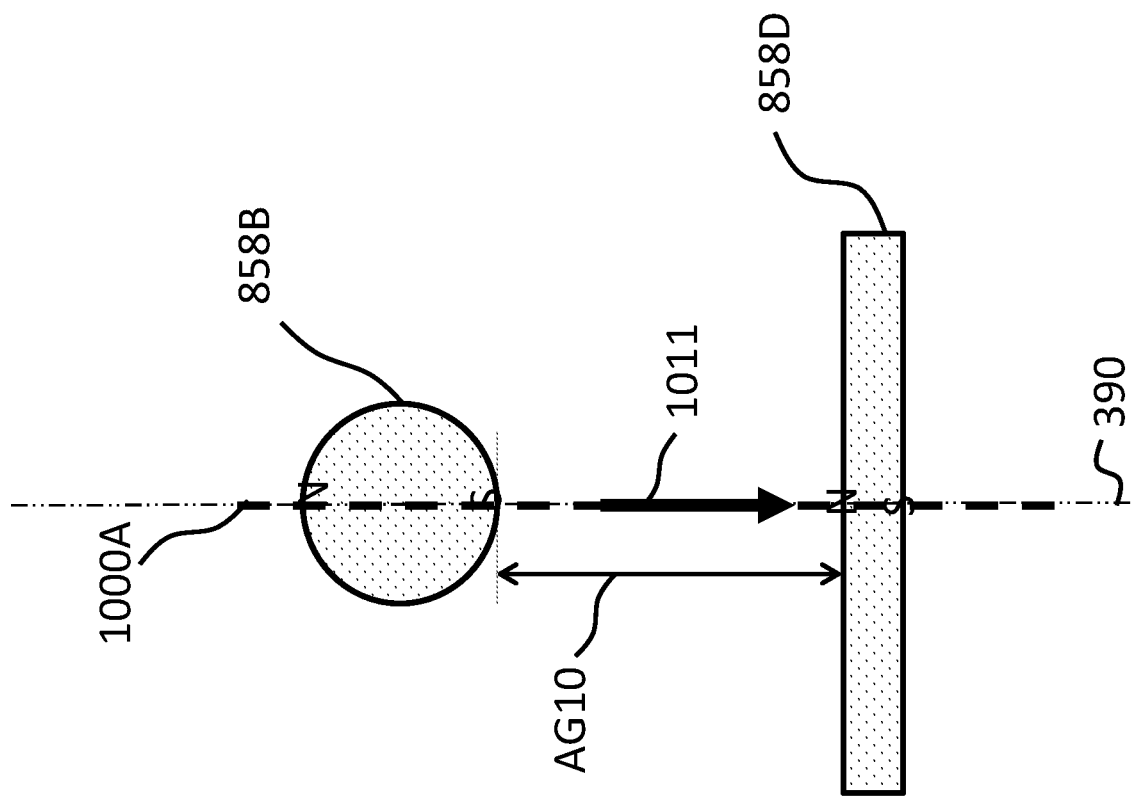
FIGS. 11A-11C are schematic diagrams illustrating adjustment of components of an exemplary embodiment of FIG. 8.

FIG. 11A depicts a view looking right in the plane of FIG. 10 (a side view of the views of FIGS. 10 and 8). Here, the magnetic flux is represented as a plane, line 1000A lying in the plane. To be clear, in these embodiments, the magnetic flux does not lie only in a plane. However, these figures are presented for conceptual purposes so as to better explain the general phenomenon associated with these embodiments. As can be seen, the plane in which the magnetic flux lies (line 1000A) is a vertical line that passes through the centers of the magnets 858B and 858D, owing to the fact that the poles of the magnets are aligned in the vertical direction. Conceptually speaking, the view of FIG. 11A represents the fact that the magnetic flux between the magnet 858B and 858D is generally vertical, as represented by the vertical line 1000A.

Figure 11B:
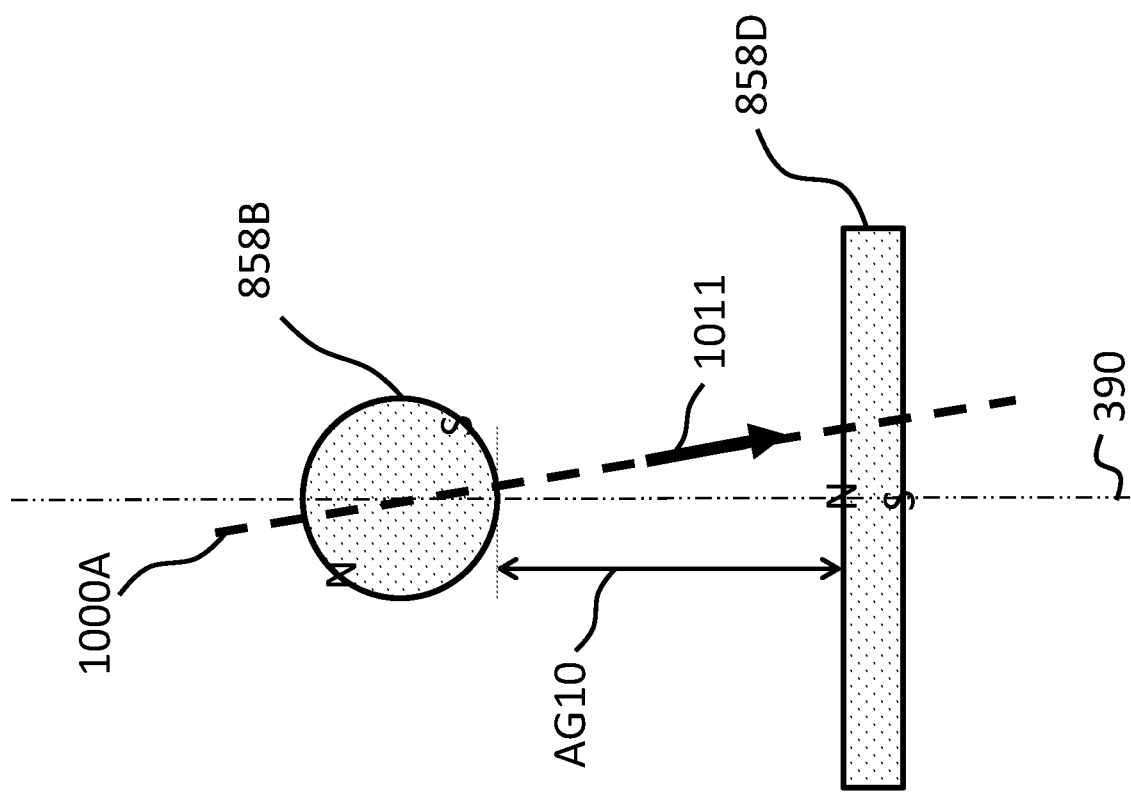
Figure 11C:
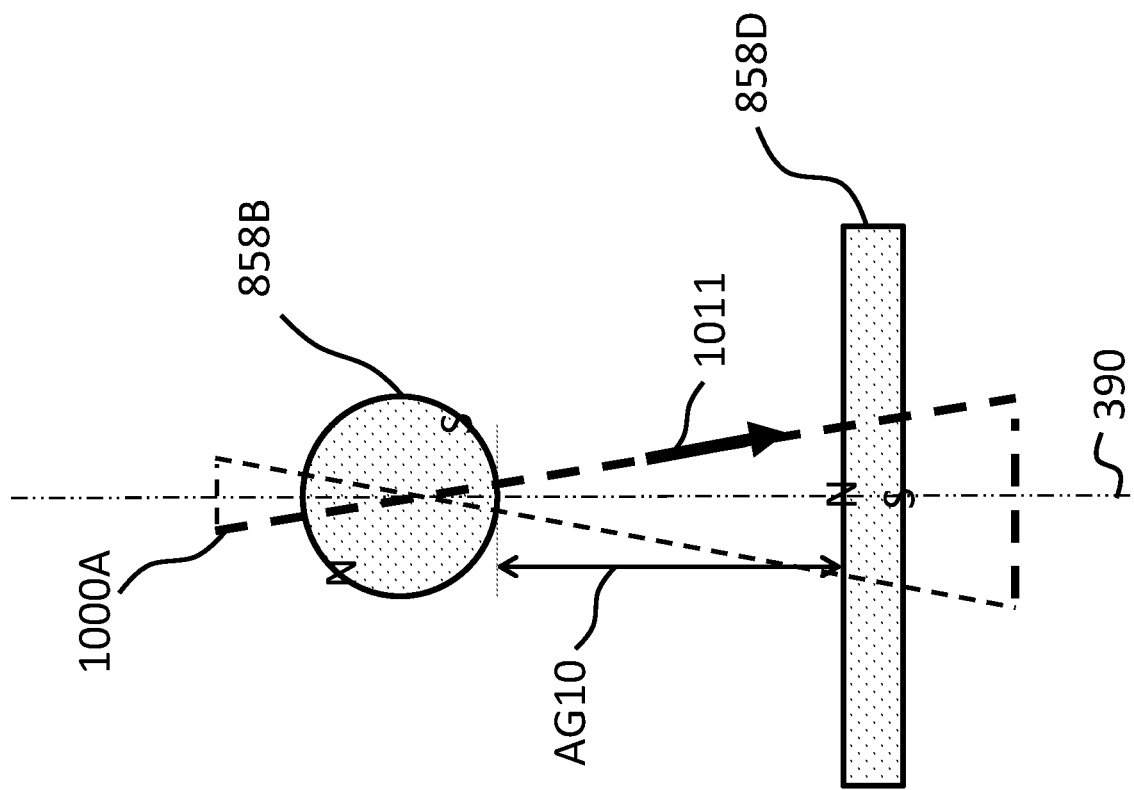

FIG. 11B conceptually represents what happens to the magnetic flux path when the magnet 858B is rotated such that the poles no longer align with the poles of magnet 858D. As can be seen, the flux path represented by line 1000A is angled relative to the vertical/relative to the longitudinal axis 390. FIG. 11B conceptually depicts the influence on the magnetic flux of magnet 858D. In this regard, as can be seen, line 1000A is not perfectly aligned with the North-South polar axis, but instead is located at an angle thereto. Again this is conceptual. The point is that the rotation of the magnet 858B changes the magnetic flux path. The changes in the magnetic flux path result in a change in the retention force/attraction force between the external magnet assembly 858EX and the implantable magnet assembly 858IM. Here, the more that the magnet 858B is rotated from the original orientation of the poles of FIG. 11A, the greater the reduction in the magnetic force attraction between the external component and the implantable component. In the embodiment depicted in FIG. 11B, the magnets of the external magnet assembly 858EX are both rotated in the same direction, and thus the path is moved in the same plane, conceptually speaking. FIG. 11C depicts the alternate scenario where the magnets of the external magnet assembly 858EX are rotated in different directions. The resulting magnetic flux path takes on the form of a piece of twisted rectangular cardboard, again, conceptually speaking (where the view of FIG. 11C is looking down the length of the flexed cardboard, where the thicker line 1000A represents the end of the piece of cardboard closest to the viewer, and the thinner line 1000A represents the end of the piece of cardboard furthest from the viewer).

In FIGS. 11A-11C, the shortened length of arrow 1011 represents the weakened retention force resulting from the movement of the path of the magnetic flux.

In at least some exemplary embodiments, the bone conduction device is configured such that when the implantable component interacts with the magnetic flux of the external component to establish retention of the external component to the recipient, a torque applied to skin of the recipient is substantially constant through a substantial range of adjustments of the path of the generated magnetic flux. In at least some exemplary embodiments, this is achieved by utilizing the two pole magnet system (e.g., where the implant has two or more magnets and the external component includes two or more magnets). In this regard, in at least some exemplary embodiments of the embodiment of FIG. 3, the tilting of the external magnet assembly 358EX can impart a torque onto the skin of the recipient because there is a stronger attraction on one side of the other side of the external component owing to the movement of the path of the magnetic flux. This torque could result in the shifting of the orientation of the external component relative to the implantable. This could have a deleterious effect respect to the use of the teachings detailed herein with a transcutaneous coil, such as an inductance coil, such as may be used in the case of a cochlear implant, or the like. This could potentially cause misalignment between the coils that are implanted in the recipient and the coils of the external component. Accordingly, in an exemplary embodiment, utilizing a plurality of magnets with orientations that are all adjustable/magnets that are all tiltable can be utilized to counteract the resulting imbalance in the forces, thus preventing the development of the aforementioned torque.

It is noted that the aforementioned torque applied to the skin that is prevented from being applied in at least some exemplary embodiments, exists both with respect to torque applied about an axis normal to the skin of the recipient and applied about axis that is parallel to and lying on the skin of the recipient, while in other exemplary embodiments, it exists on one and not the other (about the normal axis or about the parallel axis).

FIG. 12 presents another alternate embodiment utilizing magnet pairs. This exemplary embodiment has utilitarian value in that the magnet pairs counteract any imbalance in the force that results from the rotation of the magnets, thus preventing the aforementioned torque from being applied to the skin of the recipient/improving the likelihood that the external component will remain aligned with the implantable component.

More specifically, FIG. 12 depicts a schematic of an exemplary bone conduction device 1200A corresponding to bone conduction device 300 of FIG. 2. In this exemplary embodiment, the implantable component 350A of bone conduction device 1200A is the same as that of the bone conduction device 800A. Conversely, the external component 1240A has a different configuration than that of external component 840A. Briefly, four permanent magnets that generate, at least in part, the magnetic flux that is utilized to retain the external component 1240A to the recipient are located to the sides of transducer 342A. In an exemplary embodiment of this exemplary embodiment, at least some of the magnets are rotated in a plane parallel with the axis of the attraction force, to vary the path of the magnetic flux and thus vary the attraction force. At least some of the magnets are adjustable/rotatable about an axis (990 as seen in FIGS.

13A-13B, discussed below) that is perpendicular to the longitudinal axis 390 and extends through the magnets of the external magnet assembly.

External component 1240A includes an external magnet assembly that includes permanent magnets having a North-South alignment. These magnets are locationally adjustable relative to one another, as will be detailed below. However, in the configuration depicted in FIG. 12 (without adjustment), the magnets on one side of the magnetic assembly, relative to the longitudinal axis 390 of the bone conduction device 300A, all have North poles facing away from the skin of the recipient, and the magnets on the other side of the magnetic assembly relative to longitudinal axis 390 of the bone conduction device all have North poles facing towards the skin of the recipient. That is, the North-South alignment of one side of the external magnet assembly is opposite that of the other side of the assembly. However, exemplary embodiments of the external component 1240A are configured such that the individual magnets can be moved so that the poles are different than that depicted in FIG. 12.

The external magnetic assembly of external component 1240A comprises four (4) different magnets arrayed on opposite sides of the longitudinal axis 390 in two sets. (It is noted that in alternative embodiments, more magnets can be used). The first set includes outer permanent magnet 1258AO and inner permanent magnet 1258AI. The second set includes outer permanent magnet 1258BO and inner permanent magnet 1258BI. As will be detailed more thoroughly below, one or both of the outer permanent magnets of these sets are configured to be moveable relative to the inner permanent magnets of the sets, and/or visa-versa, so as to vary the path of the magnetic flux generated by the external magnetic assembly as a result of the polar axis being shifted. In this regard, in at least some exemplary embodiments, during operational use of the bone conduction device 1200A, the magnets of the external magnet assembly are aligned with the magnets of the implantable magnet assembly such that the poles of the permanent magnets 1258AO, 1258AI and 858C have a North-South alignment in exactly the same direction, and the poles of the permanent magnets 1258BO, 1258BI and 858D have a North-South alignment in the same direction (but opposite of that of magnets 1258AO, 1258AI and 858C) in a scenario where maximum attractive force between the external component 840A and the implantable component 850A is desired. Conversely, in at least some exemplary embodiments, during operational use of the bone conduction device 1200A, the magnets of the external magnet assembly are aligned with the magnets of the implantable magnet assembly such that the poles of the permanent magnets 1258AO and/or 1258AI are aligned in a different direction than that of magnet 858C due to the adjustability of the relative position of the magnets 1258AO and/or 1258AI. Furthermore, in this exemplary embodiment, during operational use of the bone conduction device 1200A, the magnets of the external magnet assembly are aligned with the magnets of the implantable magnet assembly such that the poles of the permanent magnets 858BO and/or 858BI are aligned in a different direction than that of magnet 858D because of the adjustability of the relative position of the magnets 1258BO and/or 1258BI.

Figure 13A:
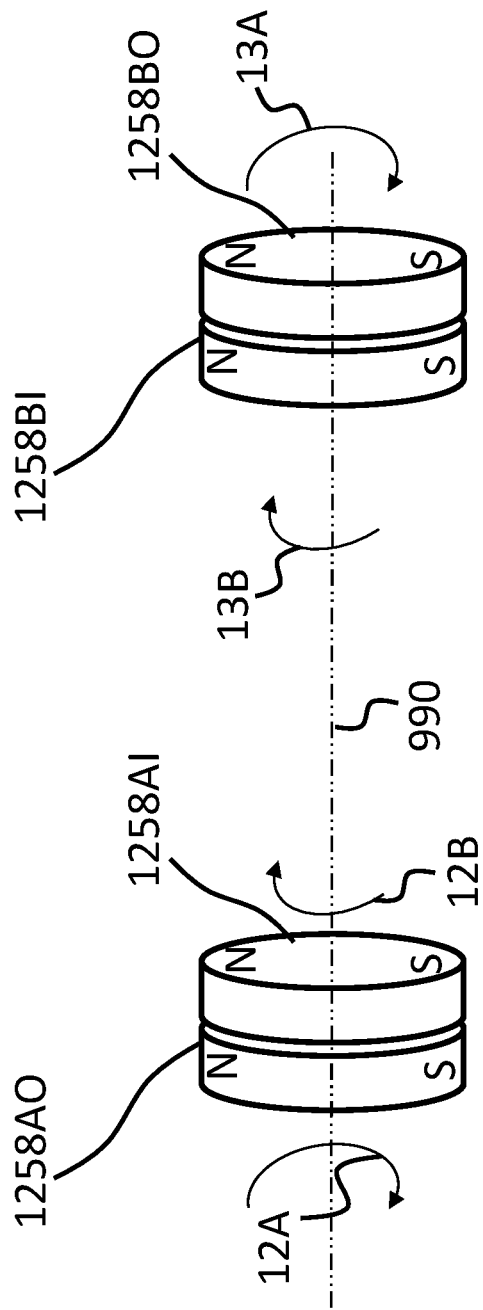
FIGS. 13A-13B depict exemplary magnet configurations of the exemplary embodiment of FIG. 12.
Figure 13B:
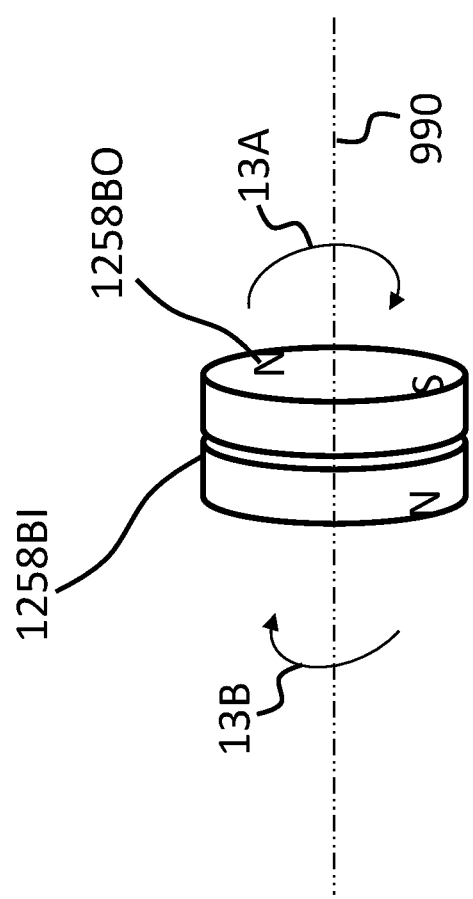

The above adjustability can be conceptually seen in FIGS. 13A-B, which conceptually depict isometric views of the 1258AI, 12858AO, 1258BI and 12858BO magnets of the bone conduction device 1200A at various orientations relative to one another. More specifically, FIG. 13A depicts a configuration of the magnets of the external magnet assembly such that the maximum attraction force between the external component 1240A and 850A is achieved.

As can be seen in FIG. 13A, the magnets of the external component are segmented into two magnets, both of which are disk shaped. Briefly, it is noted that in at least some embodiments, the configurations of magnets 1258AI and 1258AO corresponds to that of 1258BI and 1258BO, respectively, except the orientation relative to one another and relative to the longitudinal axis is reversed (1258AO is on the outside, and the South poles of both magnets 1258AI and 1258AO are located on the top (facing away from the skin). While disk magnets are depicted in the embodiment of FIG. 12, in alternative embodiments, box magnets and/or bar magnets can be used, totality or in combination with other types.

In embodiments corresponding to FIGS. 13A-13B, the external component 1240A is configured such that one or more of the outer magnets 1258AO and 1258BO can be moved to have a different angular configuration relative to the inner magnets 1258AI and 1258BI (or visa-versa, or both can be moved in some other embodiments). Accordingly, FIG. 13B depicts the outer magnet 1258BO shifted by an angle 20 degrees in the direction of arrow 13A relative to the location of those magnets depicted in FIG. 13A, and inner magnet 1258BI shifted by an angle 20° in the direction of arrow 13B. (Not shown in FIG. 13B is outer magnet 1258AO shifted in the direction of angle 12A and inner magnet 1258AI shifted in the direction of angle 12B).

Figure 14A:
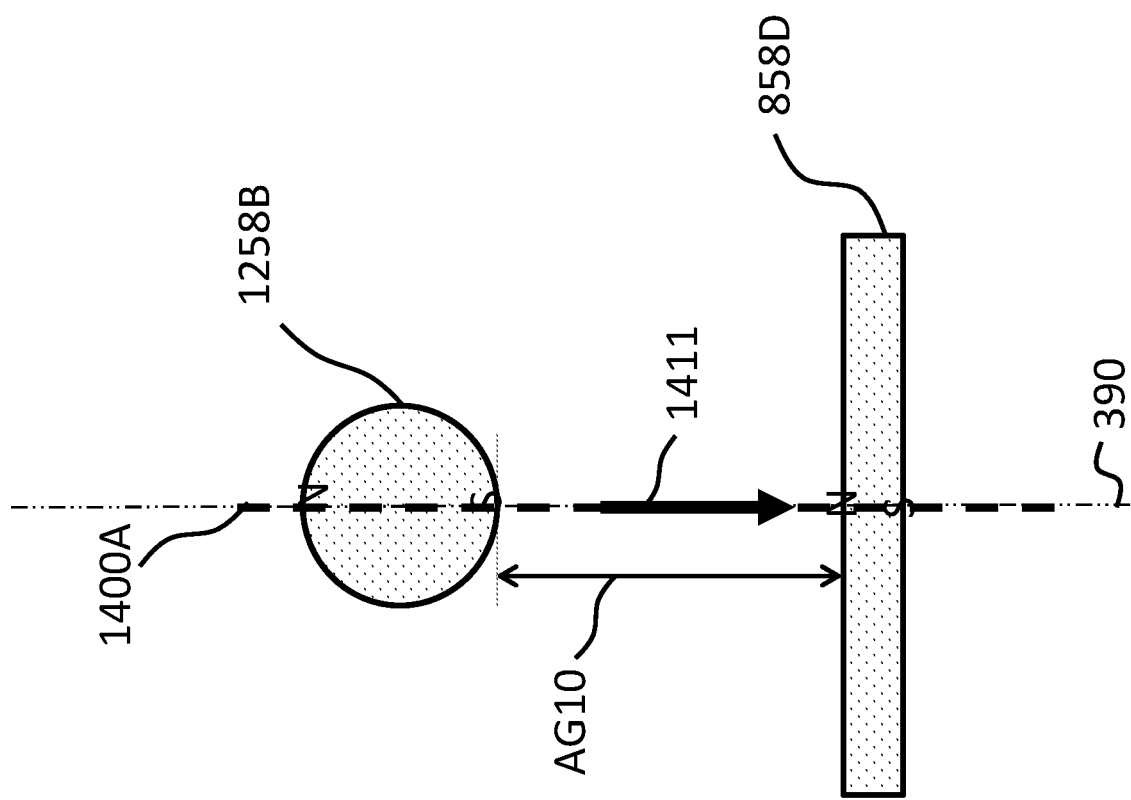
FIGS. 14A-14B depict exemplary conceptual magnetic flux paths according to an exemplary embodiment.
Figure 14B:
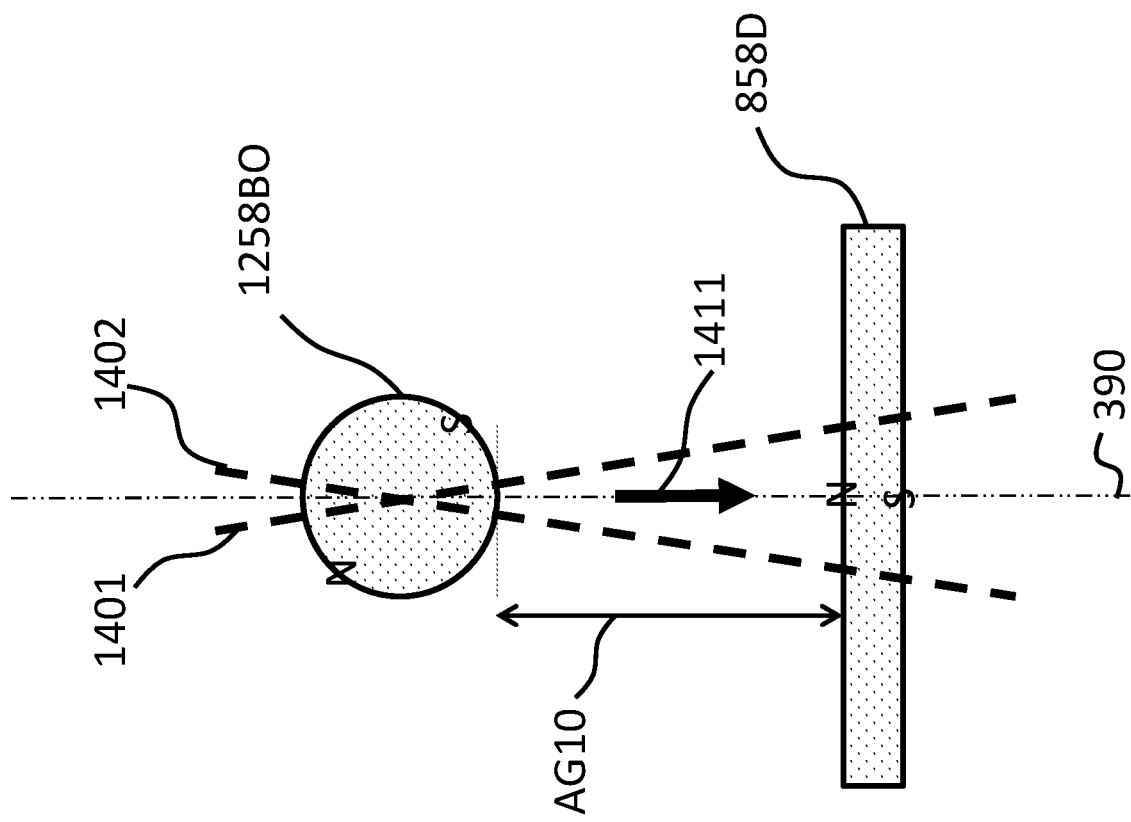

FIG. 14A conceptually represents the magnetic flux as seen looking from the side of the orientation of FIG. 12 (FIG. 14A corresponds to the view of FIG. 11A detailed above). Arrow 1411 represents the strength of the resulting magnetic flux where the poles of the magnets of the external magnet assembly 1258EX are all aligned with those of the implantable magnet assembly 858IM. FIG. 14B conceptually represents the magnetic flux as seen from the side of the orientation of FIG. 12, except with the permanent magnets are rotated according to that depicted in FIG. 13B. Line 1401 corresponds to the portion of the magnetic flux that is most influenced by magnet 1259BO (shown), and line 1402 corresponds to the portion of the magnetic flux that is most influenced by magnet 1258BI (eclipsed by magnet 1259BO). Arrow 1411 represents the weakening of the attraction force between the external component and the implantable component resulting from the varying of the magnetic flux path that results from rotation of the permanent magnet of the external component. As can be seen, the arrow 1411 in FIG. 14B is aligned with the axis 390, thus conceptually representing the lack of torque resulting from the rotation of the magnets.

Figure 15A:
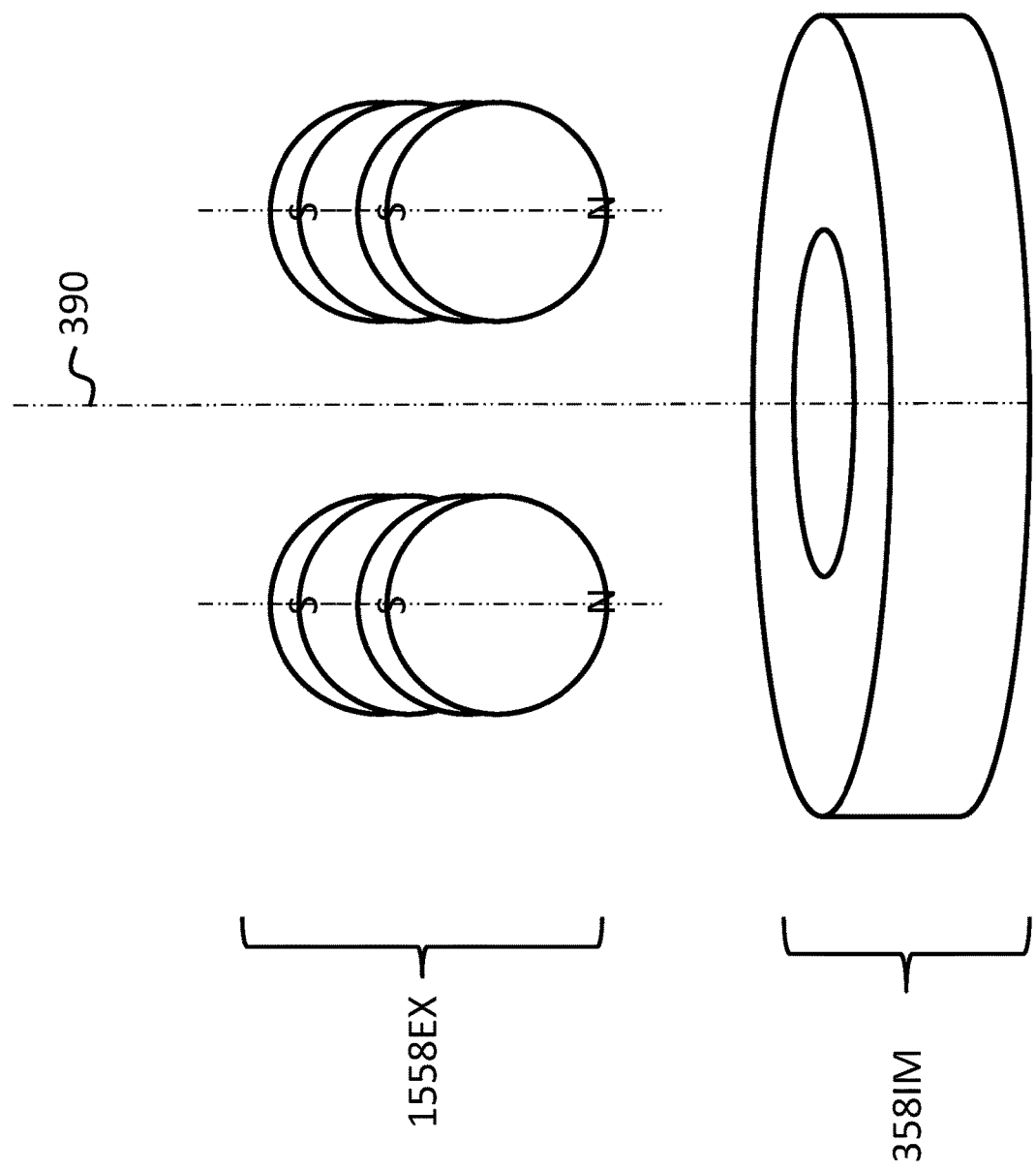
FIGS. 15A-15D depict another exemplary embodiment.

FIG. 15A depicts an exemplary embodiment where the external component includes an external magnet assembly 1558EX including four (4) permanent magnets arrayed symmetrically about the longitudinal axis 390 of the external component in 2 dimensions (as opposed to the 1 dimension of FIG. 12). In an exemplary embodiment, this configuration also prevents the development of the aforementioned torque/aids in preventing misalignment between the external component implantable component. In this exemplary embodiment, a single pole implantable magnet assembly 358IM is used (the implantable component is the same as that of the embodiment of FIG. 3 above).

Figure 15B:
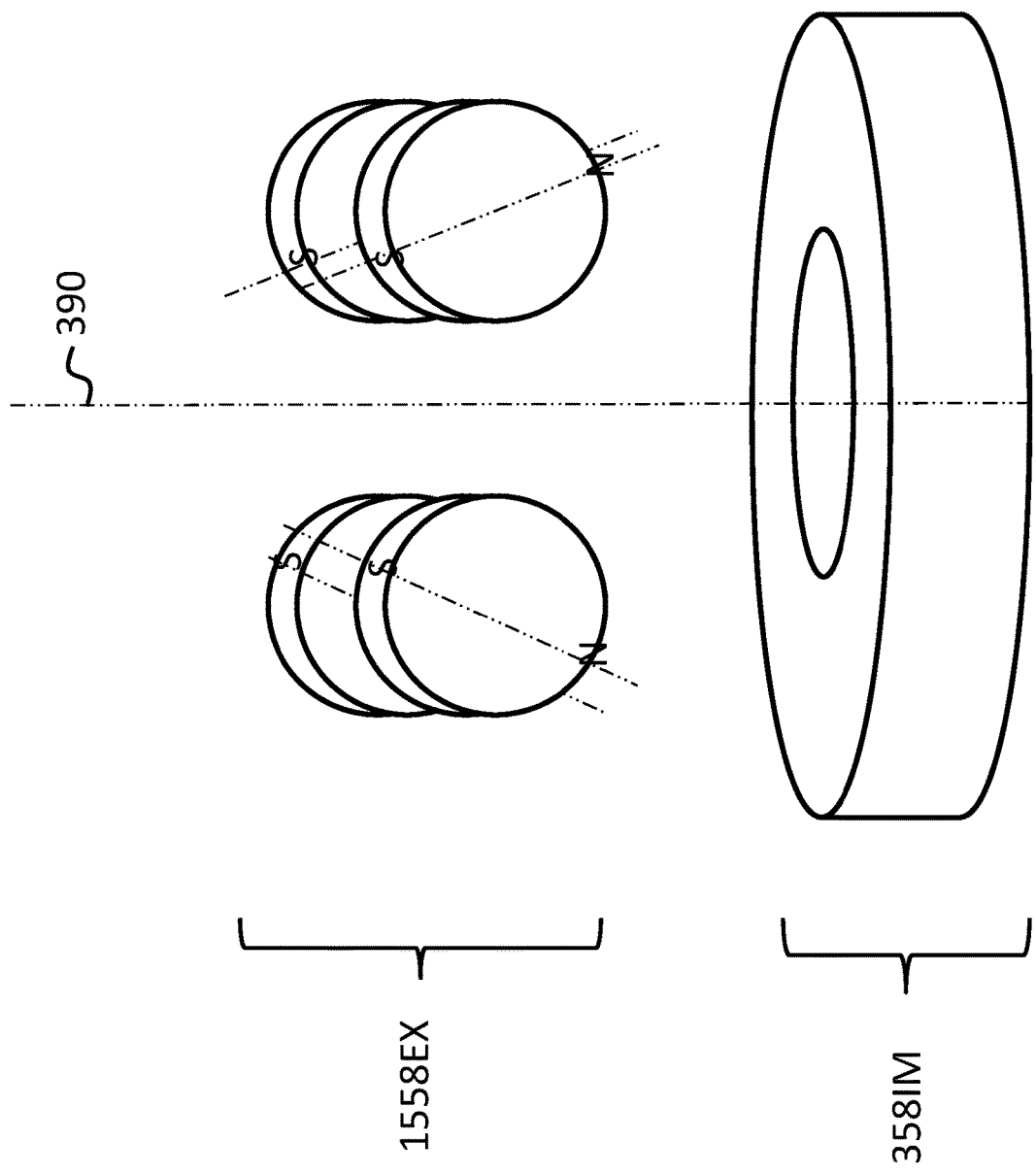

FIG. 15B schematically depicts rotation of the permanent magnets of the external magnet assembly 1558EX in a manner that results in a balance/symmetrical force distribution about axis 390, albeit one that has a reduced retention force relative to that which is the case with the magnets aligned as shown in FIG. 15A only to movement of the path of the magnetic flux. It is noted that in alternative embodiment, instead of rotation, the permanent magnets of the external magnet assembly 1558EX can tilt to change the path of the magnetic flux, and thus reduce the strength of the resulting attraction between the external component and the implantable component. Still further, in an exemplary embodiment, the permanent magnets of the external magnet assembly 1558EX can tilt and rotate to change the path of the magnetic flux, and the vary the force of the attraction between the external component and the implantable component.

In an exemplary embodiment, the permanent magnets of the external magnet assembly 1558EX are mechanically linked such that all magnets rotate and/or tilt by the same amount, albeit some in different directions. In an exemplary embodiment, the magnets of the external magnet assembly interact with a shaft having teeth are utilized to rotate and/or tilt the magnets by moving the shaft up and down. Alternatively, the shift can be aligned horizontally such that moving the shaft and the horizontal plane rotate and/or tilt the magnet. A rack and pinion system can be utilized. Alternatively and/or in addition to this, an electromagnetic actuator can be utilized. In some embodiments, each individual magnet can be rotated/tilted independently of the others. Any device, system and/or method that can enable rotation and/or tilting of the permanent magnets that can enable the teachings detailed herein and/or variations thereof to be practiced can be utilized in at least some embodiments.

Figure 15C:
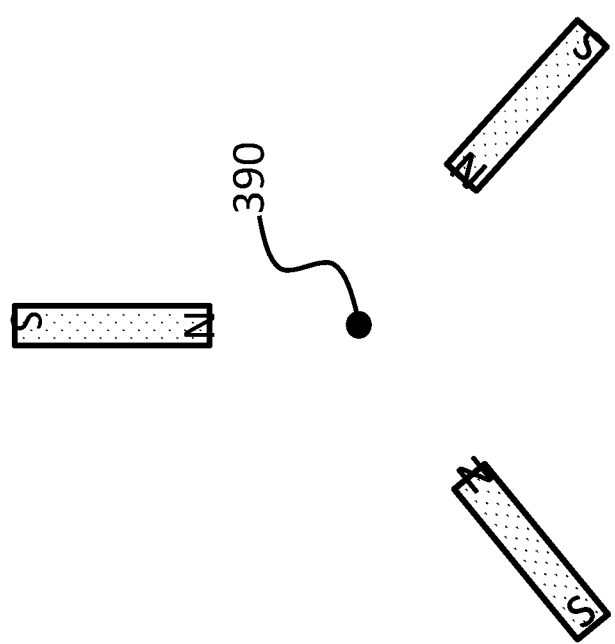
Figure 15D:
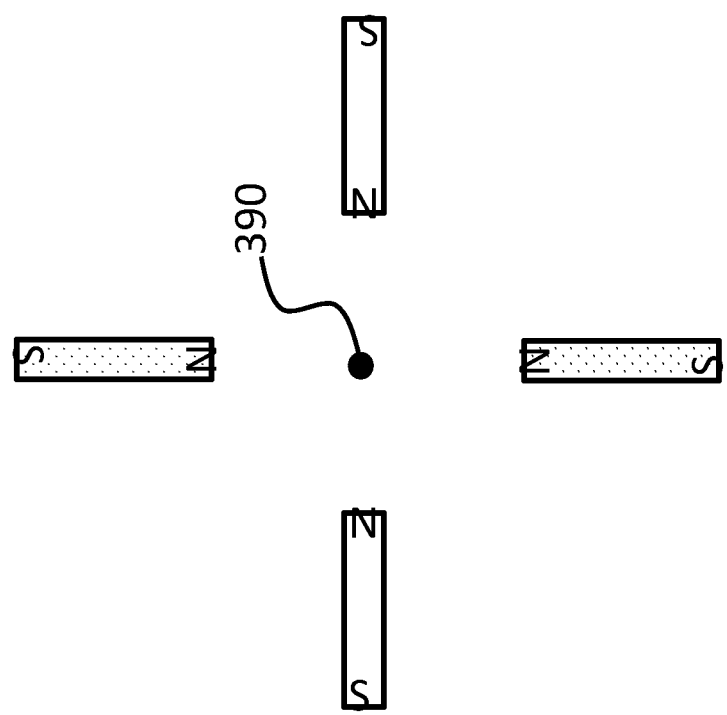

It is noted that while FIG. 15A depicts four (4) magnets of the external magnet assembly 1558EX, in an alternate embodiment, three (3) magnets are utilized. Any arrangement that will enable force balance/the elimination of torque (about various axes as detailed herein) can be utilized in at least some embodiments. For example, while the magnets of 1558EX are arrayed about axis 390 in a equidistant manner (approximately 90 degrees), with the flat faces thereof parallel to one another, in an alternate embodiment, the magnets of 1558 EX (three or four) can be arrayed as seen in FIGS. 15C and 15D, which is a view looking downward along axis 390 (FIG. 15C showing a 3 magnet configuration, and FIG. 15D showing a 4 magnet configuration), with the magnets rotated at a somewhat extreme angle (for purposes of illustration only) relative to a North-South pole alignment parallel to axis 390.

In view of the above, in an exemplary embodiment, there is an external component of a medical device, comprising a first permanent magnet having a first polarity axis, wherein the external component is configured such that the first permanent magnet contributes to the resulting magnetic retention force so as to at least partially removably retain, via the resulting magnetic retention force, the external component to a recipient thereof. The external component of the medical device comprises a second permanent magnet having a second polarity axis, wherein the external component is configured such that the second permanent magnet contributes to the resulting magnetic retention force so as to at least partially removably retain, via the resulting magnetic retention force, the external component to a recipient thereof. The external component is configured to enable the adjustment of an orientation of the second polarity axis. The external component of the medical device includes a third permanent magnet having a third polarity axis, wherein the external component is configured such that the third permanent magnet contributes to the resulting magnetic retention force so as to at least partially removably retain, via the resulting magnetic retention force, the external component to a recipient thereof. The external component is configured to enable the adjustment of an orientation of the third polarity axis. The external component of the medical device includes a fourth permanent magnet having a fourth polarity axis, wherein the external component is configured such that the fourth permanent magnet contributes to the resulting magnetic retention force so as to at least partially removably retain, via the resulting magnetic retention force, the external component to a recipient thereof, and the external component is configured to enable the adjustment of an orientation of the fourth polarity axis.

In an exemplary embodiment, there is a medical device as detailed herein, wherein the device is configured such that a resulting magnetic flux of the external component establishing the resulting magnetic retention force is substantially symmetrical about a plane parallel to a longitudinal axis of the external component throughout a range of orientations of the polar axes of the first, second third and fourth permanent magnets. Still further in an exemplary embodiment, the medical device configured such that a resulting magnetic flux of the external component establishing the resulting magnetic retention force is substantially symmetrical about the longitudinal axis of the external component throughout a range of orientations of the polar axes of the first, second, third, and fourth permanent magnets.

Figure 16:
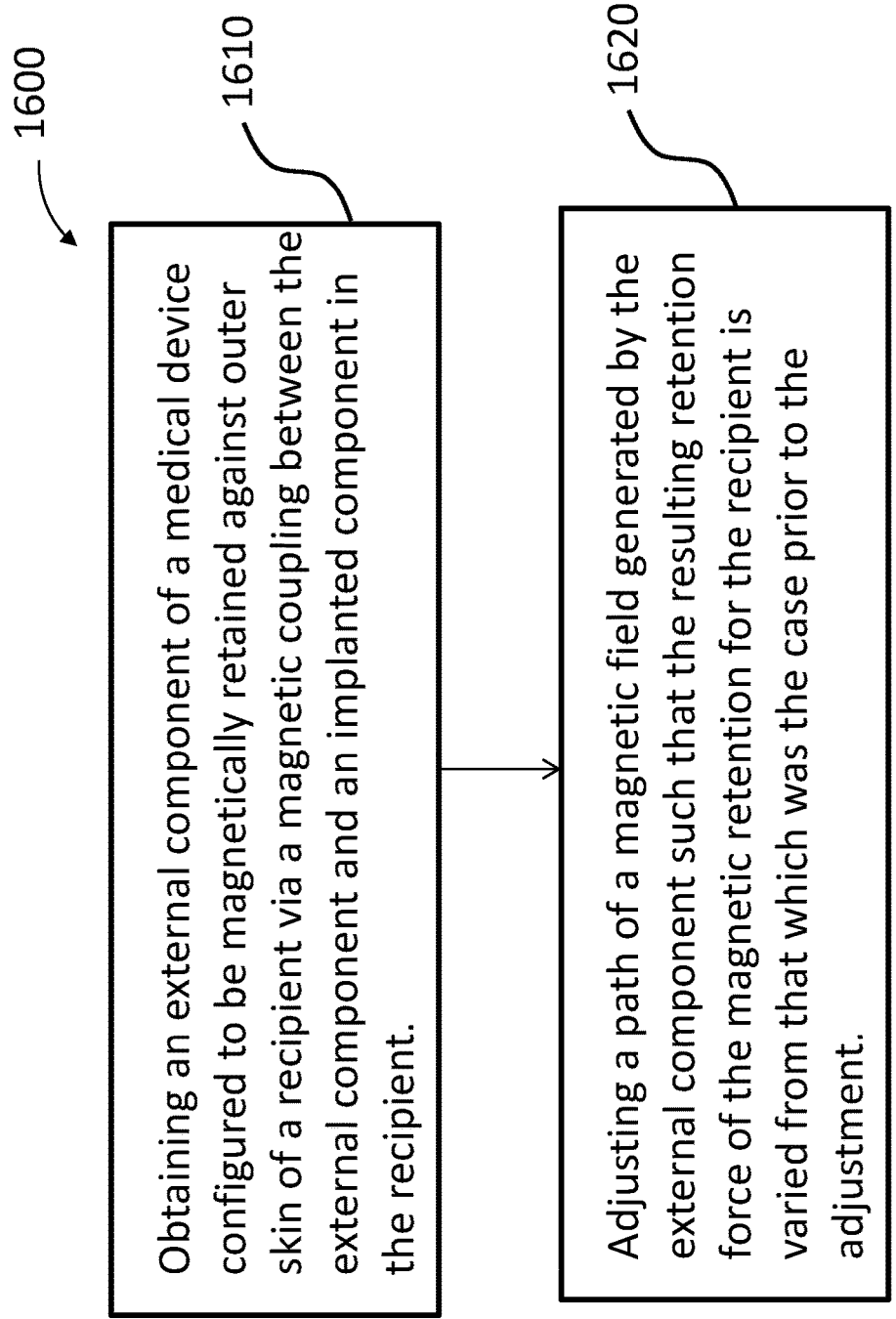
FIG. 16 depicts an exemplary flowchart for an exemplary method.

Embodiments include methods of using the medical devices detailed herein. For example, referring now to FIG. 16, there is an exemplary flowchart 1600 for an exemplary method. Method 1600 includes method action 1610, which entails the action of obtaining an external component of a medical device (e.g., 340A, 840A, 1240A, etc.) configured to be magnetically retained against outer skin of a recipient via a magnetic coupling between the external component and an implanted component (e.g. 350A, 850A, etc.) in the recipient. Method 1600 further includes method action 1610, which entails adjusting a path of a magnetic flux generated by the external component such that the resulting retention force of the magnetic retention for the recipient is varied from that which was the case prior to the adjustment. In an exemplary embodiment, this adjustment of the path of the magnetic flux results from tilting and/or rotation of the magnets as detailed herein and/or variations thereof.

In an exemplary embodiment, the aforementioned method further includes placing the external component against a recipient's skin at least one of after or during adjusting the path, such that the external component is retained against the skin of the recipient via the magnetic coupling between the external component and the implanted component, wherein the implanted component includes a magnet arrangement having a single polarity axis, and the magnetic coupling results in substantially no torque on the external component while positioned against the skin of the recipient in the absence of external forces on the external component.

In an exemplary embodiment, there is a method that includes placing the external component against a recipient's skin at least one of after or during adjusting the path of the magnetic flux such that the external component is retained against the skin of the recipient via the magnetic coupling between the external component and the implanted component, wherein the implanted component includes a magnet arrangement having a single polarity axis, and the resulting magnetic flux of the magnetic flux generated by the external component and the magnet of the implanted component is symmetrical about a plane parallel to and lying on the single polarity axis.

In an exemplary embodiment, there is a method that includes placing the external component against a recipient's skin at least one of during or after adjusting the path such that the external component is retained against the skin of the recipient via the magnetic coupling between the external component and the implanted component, wherein the implanted component includes a magnet arrangement having multiple polarity axes, and the resulting magnetic field of the magnetic flux generated by the external component and the implanted component is symmetrical about a plane parallel to and lying in between respective axes of the multiple polarity axes.

Still further, in at least some embodiments, the action of adjusting the orientation of the polar axes of one or more magnets of the external component such that the resulting retention force is varied due to a variation in the path of the magnetic flux is executed without changing a total magnetic density of permanent magnets of the external component. In at least some embodiments, the action of adjusting the orientation of one or more polarity axes of the magnets of the external component such that the resulting retention force is varied is executed without removing or adding any magnets to the external component and/or the action of adjusting the orientation of one or more of the polar axes of the magnets of the external component is executed without directly accessing the one or more magnets from outside the external component.

Also, it is noted that while the embodiments detailed above are directed towards an arrangement where the external component includes the adjustable magnet arrangement, in at least some alternate embodiments, the implantable component can include the adjustable magnets. That is, in at least some embodiments, any one or more or all of the teachings detailed herein are applicable to the implantable component(s) detailed herein. It is further noted that in some embodiments, both the implantable component and the external component can utilize the adjustable features detailed herein.

In an exemplary embodiment, the implanted magnets can be hermetically sealed within an implantable housing. In some embodiments, a magnetic field can be utilized to adjust the location of the magnets. Alternatively and/or in addition to this, an invasive surgical procedure can be utilized, albeit a limited one. In an exemplary embodiment, the procedure can be of limited invasivity such that a local anesthesia need only be utilized (if at all). For example, a needle can be inserted through the skin to contact the implant and push and/or pull a portion of the implanted component, thereby moving the magnet(s). Alternatively, a puncture can be made in the skin, and a thin rod or the like can be inserted through the puncture to apply the tensile and/or compressive force to the implantable component so as to move the magnet(s). An exemplary embodiment can include a lock that can be disabled and enabled with the needle/rod, which permits and prevents, respectively, movement of the magnet(s).

It is noted that any disclosure of any device detailed herein corresponds to a disclosure of a method of making that device and a method of utilizing the device. It is further noted that any disclosure of any method detailed herein corresponds to a disclosure of a device utilized to execute that method. Any feature of any embodiment detailed herein can be combined with any other feature of any other embodiment detailed herein unless otherwise specified.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A medical device, comprising:
an implantable component; and
an external component, wherein
the implantable component includes a first magnet assembly including at least a first magnet having a first polarity axis and a second magnet having a second polarity axis, wherein the first polarity axis has an angular offset relative to a longitudinal axis of the first magnet assembly, wherein the second polarity axis has an angular offset relative to the longitudinal axis of the first magnet assembly, and wherein the angular offsets are held constant relative to the longitudinal axis of the first magnet assembly,
the external component includes a second magnet assembly, and
the external component is configured to be magnetically retained against outer skin of a recipient of the medical device via a magnetic coupling between the external component and the implantable component when the implantable component is implanted in the recipient.

2. The medical device of claim 1, wherein:
the second magnet assembly includes a magnet that has a North-South alignment that is normal to a longitudinal axis of the second magnet assembly.

3. The medical device of claim 1, wherein:
the second magnet assembly includes a third magnet having a third polarity axis and a fourth magnet having a fourth polarity axis, wherein the third polarity axis has an angular offset relative to a longitudinal axis of the second magnet assembly, and wherein the fourth polarity axis has an angular offset relative to the longitudinal axis of the second magnet assembly.

4. The medical device of claim 1, wherein:
the second magnet assembly includes a third magnet having a third polarity axis and a fourth magnet having a fourth polarity axis, wherein the third polarity axis is parallel to a longitudinal axis of the second magnet assembly, and wherein the fourth polarity axis is parallel to the longitudinal axis of the second magnet assembly.

5. The medical device of claim 1, wherein:
when the longitudinal axis of the first magnet assembly is concentrically aligned with a longitudinal axis of the second magnet assembly when the external component is magnetically retained against outer skin of the recipient via the magnetic coupling, the first polarity axis has an angular offset to a third polarity axis of a magnet of the second magnet assembly.

6. The medical device of claim 1, wherein:
when the external component is magnetically retained against outer skin of the recipient via the magnetic coupling, the first magnet assembly and the second magnet assembly establish a magnetic flux circulation path on a plane that is parallel to and lying on the longitudinal axis of the first magnet assembly that is asymmetrical about a second plane normal to the longitudinal axis of the first magnet assembly and normal to the plane.

7. The medical device of claim 1, wherein:
the first magnet is spaced away from the second magnet.

8. The medical device of claim 1, wherein:
the first magnet assembly includes only the first magnet and the second magnet.
9. The medical device of claim 1, wherein:
the first magnet assembly includes only the first magnet and the second magnet; and
the first magnet assembly is located in a hermetically sealed housing.
10. The medical device of claim 1, wherein:
the medical device is configured to evoke a hearing percept;
the medical device includes a microphone; and
the medical device includes a sound processor.
11. An medical device, comprising:
an implantable component; and
an external component, wherein
the external component includes a first magnet assembly including at least a first magnet having a first polarity axis and a second magnet having a second polarity axis, wherein the first polarity axis has an angular offset relative to a longitudinal axis of the first magnet assembly, wherein the second polarity axis has an angular offset relative to the longitudinal axis of the first magnet assembly, and wherein the angular offsets are fixed relative to the longitudinal axis of the first magnet assembly,
the implantable component includes a second magnet assembly, and
the external component is a medical device configured to be magnetically retained against outer skin of a recipient of the medical device via a magnetic coupling between the external component and the implantable component when the implantable component is implanted in the recipient.
12. The medical device of claim 11, wherein:
the first magnet assembly includes a magnet that has a North-South alignment that is normal to the longitudinal axis.
13. The medical device of claim 12, wherein:
the second magnet assembly includes a third magnet having a third polarity axis and a fourth magnet having a fourth polarity axis, wherein the third polarity axis has an angular offset relative to a longitudinal axis of the second magnet assembly, and wherein the fourth polarity axis has an angular offset relative to the longitudinal axis of the second magnet assembly.
14. The medical device of claim 11, wherein:
a value of the angular offset of the first polarity axis is the same as a value of the angular offset of the second polarity axis.
15. The medical device of claim 11, wherein:
the second magnet assembly includes a third magnet having a third polarity axis and a fourth magnet having a fourth polarity axis; and
when the longitudinal axis of the first magnet assembly is concentrically aligned with a longitudinal axis of the second magnet assembly, when the external component is magnetically retained against outer skin of the recipient via the magnetic coupling, the first polarity axis has an angular offset to the third polarity axis, and the second polarity axis has an angular offset to the fourth polarity axis.
16. The medical device of claim 11, wherein:
the first magnet is spaced away from the second magnet.
17. The medical device of claim 11, wherein:
the first magnet assembly includes only three magnets, the three magnets including the first magnet and the second magnet;
the second magnet assembly includes only two magnets; and
the second magnet assembly is located in a hermetically sealed housing.
18. The medical device of claim 11, wherein:
the first magnet assembly includes a third magnet, wherein the third magnet is in between the first magnet and the second magnet.
19. The medical device of claim 11, wherein:
the first magnet assembly includes a third magnet, wherein the third magnet includes a third polarity axis, and the third polarity axis has an angular offset from the first polarity axis and the second polarity axis.
20. The medical device of claim 11, wherein:
the medical device includes a microphone; and
the medical device includes a sound processor.
21. A component of a medical device, comprising:
a housing; and
a magnet assembly that is located in the housing, the magnet assembly comprising no more than three magnets, wherein at least one of the no more than three magnets has at least one flat face, wherein
the medical device comprises an external component and an implantable component, wherein the component of the medical device is configured to generate a magnetic flux that removably retains, via a resulting magnetic retention force, the external component to a recipient of the implantable component, the component of the medical device being one of the external component or the implantable component, and
the medical device is configured so that the magnet assembly is both tiltable and rotatable within the housing.
22. The component of a medical device of claim 21, wherein:
there are no more than two magnets in the housing.
23. The component of a medical device of claim 21, wherein:
the magnet assembly includes a magnet that has a North-South alignment that is normal to a longitudinal axis of the magnet assembly.
24. The component of a medical device of claim 21, wherein:
the component of the medical device is the external component of the medical device.
25. The component of a medical device of claim 21, wherein:
the component of the medical device is the implantable component of the medical device.
26. The component of a medical device of claim 21, wherein:
the magnet assembly includes a first magnet and at least a second magnet, wherein the component of the medical device is configured to enable the second magnet to move within the housing relative to the first magnet.
27. The component of a medical device of claim 21, wherein:
the tilting is in a plane parallel to a longitudinal axis of the housing; and
the rotating is in a plane normal to the longitudinal axis of the housing.

28. The component of a medical device of claim 21, wherein:
- the component is configured so that the magnet assembly is rotatable within the housing about a first axis and is rotatable about a second axis, wherein the first axis and the second axis intersect.

29. The component of a medical device of claim 21, wherein:
- the component is configured so that the magnet assembly is rotatable within the housing about a first axis and is rotatable about a second axis, wherein the first axis and the second axis pass through a magnet of the magnet assembly.

30. A device, comprising:
- the component of a medical device of claim 21; and
- a second component, wherein
- the device is the medical device,
- the second component is the other of the external component or the implantable component,
- the medical device includes a microphone, and
- the medical device includes a sound processor.

* * * * *